(12) United States Patent
Shigyo et al.

(10) Patent No.: US 11,270,569 B2
(45) Date of Patent: Mar. 8, 2022

(54) INFORMATION PROCESSING APPARATUS AND INFORMATION PROCESSING METHOD

(71) Applicant: SONY CORPORATION, Tokyo (JP)

(72) Inventors: Maki Shigyo, Tokyo (JP); Masanori Katsu, Tokyo (JP); Kiminobu Nishimura, Kanagawa (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 17/040,517

(22) PCT Filed: Feb. 1, 2019

(86) PCT No.: PCT/JP2019/003615
§ 371 (c)(1),
(2) Date: Sep. 22, 2020

(87) PCT Pub. No.: WO2019/187623
PCT Pub. Date: Oct. 3, 2019

(65) Prior Publication Data
US 2021/0027604 A1    Jan. 28, 2021

(30) Foreign Application Priority Data
Mar. 30, 2018  (JP) .............................. JP2018-067282

(51) Int. Cl.
*A61B 1/00*   (2006.01)
*G08B 21/18*  (2006.01)
*A61B 5/11*   (2006.01)
*A61B 5/16*   (2006.01)

(52) U.S. Cl.
CPC ............. *G08B 21/18* (2013.01); *A61B 5/1118* (2013.01); *A61B 5/165* (2013.01); *A61B 2503/40* (2013.01)

(58) Field of Classification Search
CPC .................................. A61B 1/00; G16H 10/00
See application file for complete search history.

(56) References Cited

FOREIGN PATENT DOCUMENTS

| JP | 2010-267207 A | 11/2010 |
| JP | 2010267207 A | * 11/2010 |
| JP | 2013-174846 A | 9/2013 |
| JP | 2013174846 A | * 9/2013 |
| JP | 2013-250862 A | 12/2013 |
| JP | 2018-045532 A | 3/2018 |
| JP | 2018045532 A | * 3/2018 |

OTHER PUBLICATIONS

Yuki Shitara, Study on Application Usage Monitoring for user Life Pattern Analysis, Feb. 14, 2015, IEICE Tehnical Report, vol. 114, No. 488, pp. 31-36, 1-12, ISSN 0913-5685 (Year: 2015).*
Shitara, et al., "Study on Application Usage Monitoring for User Life Pattern Analysis", IEICE Technical Report, vol. 114, No. 488, Mar. 3, 2015, pp. 31-36.
International Search Report and Written Opinion of PCT Application No. PCT/JP2019/003615, dated Mar. 5, 2019, 11 pages of ISRWO.

* cited by examiner

*Primary Examiner* — Shirley Lu
(74) *Attorney, Agent, or Firm* — Chip Law Group

(57) ABSTRACT

To provide an information processing apparatus including a processing unit that compares detected time series data and time series data stored in advance to detect unusualness, and a notification unit that controls, when the unusualness is detected by the processing unit, a timing of notification in accordance with a content of the detected unusualness.

11 Claims, 28 Drawing Sheets

FIG. 4

| Use case | Device | Sensor | Remarks |
|---|---|---|---|
| Place rareness | Wearable device/smartphone | · GPS/wifi | |
| Activity amount | Wearable device/smartphone | · Acceleration sensor<br>· Pulse (heartbeat) sensor | |
| Conversation amount | Wearable device/smartphone | · Microphone | |
| Whereabouts (whether or not a user is at a certain place) | Stationary sensor | · Human sensor/camera | The stationary sensor is assumed to be a home agent or the like. |
| Change in robot behavior | Robot | · [Amount of contact] tactile sensor/camera<br>· [Conversation amount] microphone | The amount of contact with the robot can also be determined by position information indicating whether a person is nearby. |
| Real-time friendliness for each companion | Wearable device/smartphone | · [Companion] GPS/wifi<br>· [Conversation amount] microphone | Position information is used to perform companion determination. |
| Exciting place determination | Wearable device/smartphone | · [Place rareness] GPS/wifi<br>· [Excitement degree] pulse (heartbeat) sensor | |

FIG. 5A

| Place ID | x | 1 | 2 | 3 |
|---|---|---|---|---|
| Place Name | Traveling | Home | Company | Station building |

| date | day | 7:00 | 7:30 | 8:00 | 8:30 | 9:00 | 9:30 | 10:00 | 10:30 | 11:00 | 11:30 | 12:00 | 12:30 | 13:00 | 13:30 | 14:00 | 14:30 |
|---|---|---|---|---|---|---|---|---|---|---|---|---|---|---|---|---|---|
| June 15, 2017 | Thu | 1 | x | 2 | 2 | 2 | 2 | 2 | 2 | 2 | 2 | 2 | 2 | 2 | 2 | 2 | 2 |
| June 16, 2017 | Fri | 1 | x | 2 | 2 | 2 | 2 | 2 | 2 | 2 | 2 | 2 | 2 | 2 | 2 | 2 | 2 |
| June 17, 2017 | Sat | 1 | 1 | 1 | 1 | 1 | 1 | 1 | 1 | 1 | 10 | 10 | 1 | 1 | 1 | 1 | 17 |
| June 18, 2017 | Sun | 1 | 1 | 1 | 1 | 1 | 1 | 1 | 1 | 1 | 1 | 1 | 1 | 1 | 1 | 1 | 1 |

FIG. 5B

| date | day | Home place1 | Company place2 | Station building place3 |
|---|---|---|---|---|
| June 15, 2017 | Thu | 1 | 1 | 0 |
| June 16, 2017 | Fri | 1 | 1 | 0 |
| June 17, 2017 | Sat | 1 | 0 | 1 |
| June 18, 2017 | Sun | 1 | 0 | 0 |

FIG. 5C

| date | day | 7:00 | 7:30 | 8:00 | 8:30 | 9:00 | 9:30 | 10:00 | 10:30 | 11:00 | 11:30 | 12:00 | 12:30 | 13:00 | 13:30 | 14:00 | 14:30 |
|---|---|---|---|---|---|---|---|---|---|---|---|---|---|---|---|---|---|
| June 15, 2017 | Thu | 1.07 | 1.36 | 1.66 | 1.66 | 1.66 | 1.66 | 1.66 | 1.66 | 1.66 | 1.66 | 1.66 | 1.66 | 1.66 | 1.66 | 1.66 | 1.66 |
| June 16, 2017 | Fri | 1.07 | 1.36 | 1.66 | 1.66 | 1.66 | 1.66 | 1.66 | 1.66 | 1.66 | 1.66 | 1.66 | 1.66 | 1.66 | 1.66 | 1.66 | 1.66 |
| June 17, 2017 | Sat | 1.07 | 1.07 | 1.07 | 1.07 | 1.07 | 1.07 | 1.07 | 1.07 | 1.07 | 4.50 | 4.50 | 1.07 | 1.07 | 1.07 | 1.07 | 15.75 |
| June 18, 2017 | Sun | 1.07 | 1.07 | 1.07 | 1.07 | 1.07 | 1.07 | 1.07 | 1.07 | 1.07 | 1.07 | 1.07 | 1.07 | 1.07 | 1.07 | 1.07 | 1.07 |

FIG. 6
JUNE 15, 2017
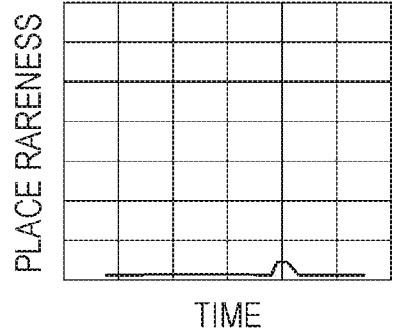
JUNE 16, 2017
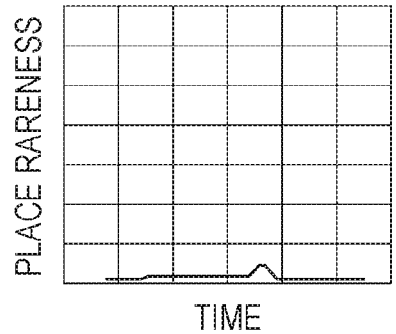
JUNE 17, 2017
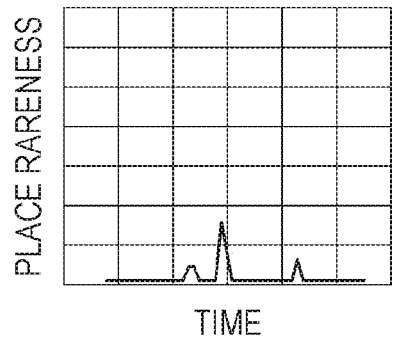
JUNE 18, 2017
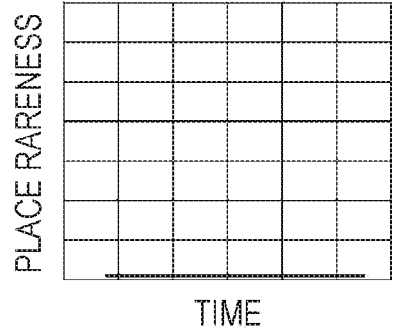

FIG. 8A
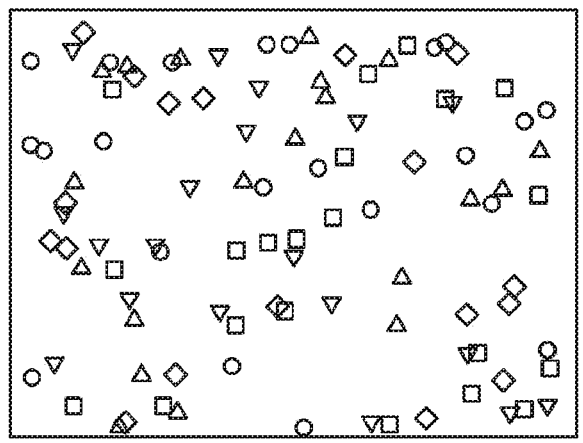
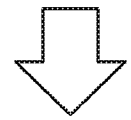
FIG. 8B
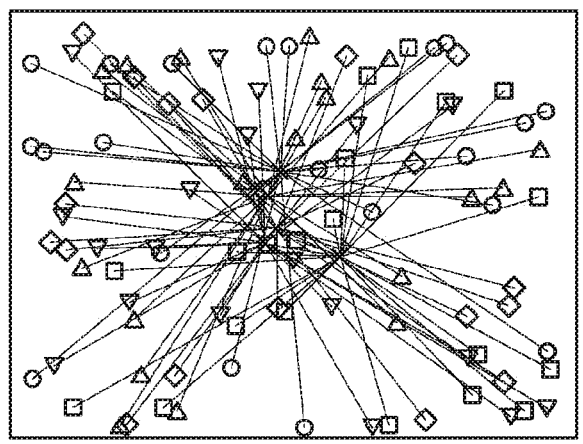
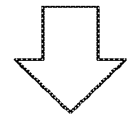
FIG. 8C
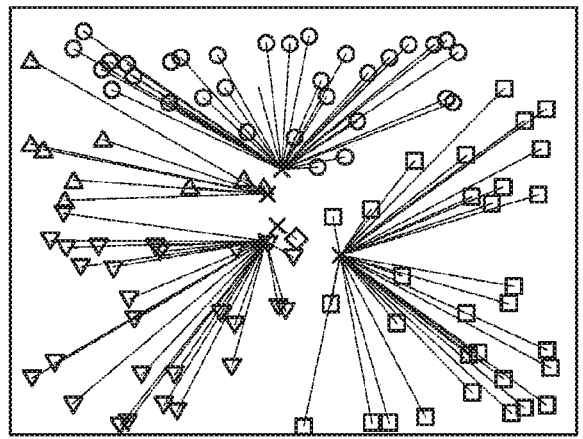

FIG. 12

| | Cluster1 | Cluster2 | Cluster3 | Cluster4 |
|---|---|---|---|---|
| The number of days applicable | 40 | 11 | 9 | 2 |
| Typical waveform | | | | |
| Characteristic | In a familiar place throughout the day (home, workplace) | In a rare place for a short time (visited a nearby place) | In a rare place for a long time (visited a faraway place) | In a rare place throughout the day (trip) |

WOULD YOU LIKE TO SHARE RECORDS OF YOUR UNUSUAL EXPERIENCE WITH YOUR FRIENDS?

CONGRATULATIONS!
YOU HAVE BEEN MORE ACTIVE THAN USUAL.

YOU HAVE HAD LESS AMOUNT OF CONVERSATION THAN USUAL.
LET'S CONSCIOUSLY COMMUNICATE WITH OTHERS.

YOUR STUDY TIME IS LESS THAN USUAL.
LET'S MAKE A HABIT OF STUDYING.

FIG. 17

| | Cluster1 | Cluster2 | Cluster3 |
|---|---|---|---|
| The number of days applicable | 20 | 3 | 1 |
| Typical waveform | date: JULY 28, 2017 | date: JULY 31, 2017 | date: AUGUST 14, 2017 |
| Characteristic | Commuting to and from work (no vigorous exercise) | Jogging after work | Jogging on a holiday |

FIG. 22
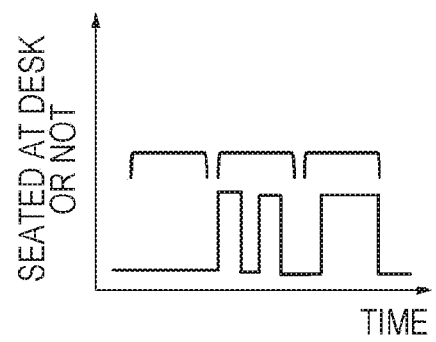
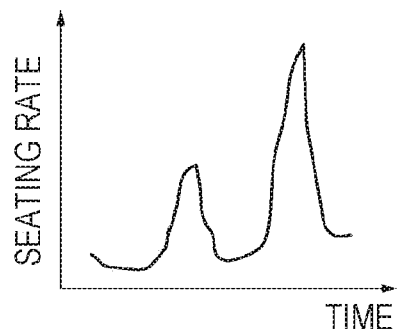

YOU ARE BEING FRIENDLIER THAN USUAL.

YOU ARE BEING LESS FRIENDLY THAN USUAL. WHAT'S THE MATTER?

YOU HAVE VISITED AN EXCITING PLACE!

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2019/003615 filed on Feb. 1, 2019, which claims priority benefit of Japanese Patent Application No. JP 2018-067282 filed in the Japan Patent Office on Mar. 30, 2018. Each of the above-referenced applications is hereby incorporated herein by reference in its entirety.

TECHNICAL FIELD

The present technology relates to an information processing apparatus, an information processing method, and a program for detecting unusualness about user's behavior.

BACKGROUND ART

Detecting unusual behavior that is differs from daily behavior of a user makes it possible to give an appropriate caution or advice to the user. Proposals have conventionally been made to detect unusualness, but the proposals are only for limited use cases and relate to a system that requires a specific sensor.

Furthermore, Patent Document 1 describes some patterns for determining unusualness. For example, in a case where there is anything extraordinary about a time period in a behavior pattern, it is determined to be unusual behavior. Furthermore, in a case where there is anything extraordinary about a type in a behavior pattern extracted from sensor information, it is determined to be unusual behavior. Specifically, in a case of a user whose "walking" behavior and "taking a train" behavior are usually extracted in the morning, if "running" behavior or "riding a bicycle" behavior is extracted, the "running" behavior or "riding a bicycle" behavior is determined to be unusual behavior. Moreover, in a case where there is anything extraordinary about a time period in an experience extracted from text information, it is determined to be unusual behavior. Specifically, in a case of a user whose "having a meal" experiences are extracted in the morning, around noon, and in the evening, if a "having a meal" experience is extracted at midnight or if no "having a meal" experience is extracted around noon, the corresponding experience is determined to be unusual behavior. Moreover, in a case where there is anything extraordinary about a type in an experience extracted from text information, it is determined to be unusual behavior. Specifically, in a case of a user whose "having a meal" experience is extracted around noon, if a "running" experience is detected around noon, the "running" experience around noon is determined to be unusual behavior.

CITATION LIST

Patent Document

Patent Document 1: Japanese Patent Application Laid-Open No. 2013-250862

SUMMARY OF THE INVENTION

Problems to be Solved by the Invention

The description in Patent Document 1 relates to detecting one-off behavior, and it has been difficult to give a meaningful notification of some kind to a user on the basis of this detection. Furthermore, whether or not something is unusual is an issue unique to the user, and it cannot be said that applying a uniform criterion to all users to determine unusualness is an appropriate approach.

It is therefore an object of the present technology to provide an information processing apparatus, an information processing method, and a program that are versatile, capable of determining unusualness on the basis of a criterion unique to an individual user, and capable of giving meaningful notifications to users.

Solutions to Problems

The present technology provides an information processing apparatus including:

a processing unit that compares detected time series data and time series data stored in advance to detect unusualness; and a notification unit that controls, when the unusualness is detected by the processing unit, a timing of notification in accordance with a content of the detected unusualness.

Furthermore, the present technology provides an information processing method including:

comparing detected time series data and time series data stored in advance to detect unusualness; and controlling, when the unusualness is detected, a timing of notification in accordance with a content of the detected unusualness.

Moreover, the present technology provides a program that causes a computer to execute an information processing method, the information processing method including:

comparing detected time series data and time series data stored in advance to detect unusualness; and controlling, when the unusualness is detected, a timing of notification in accordance with a content of the detected unusualness.

Effects of the Invention

According to at least one embodiment, a detection data acquisition unit is provided in accordance with a use case, and this enables detection of unusualness by a common algorithm and a variety of applications. Furthermore, a template can be formed as a determination criterion unique to a user, and this enables appropriate detection of unusualness. Note that the effects described here are not necessarily restrictive, and the effects of the invention may be any of the effects described in the present technology or may be effects different from those.

BRIEF DESCRIPTION OF DRAWINGS

FIG. 4 is a diagram illustrating a table for describing a device and a sensor for each use case that are used to configure the system of the present technology.

FIGS. 5A, 5B, and 5C are diagrams illustrating tables used for describing processing in a case of forming place rareness as detection data.

FIG. 6 is a diagram illustrating a specific example of a place rareness waveform.

FIGS. 8A, 8B, and 8C are diagrams used for describing clustering using k-means clustering.

FIG. 12 is a diagram illustrating an example of a daily template relating to place rareness.

FIG. 17 is a diagram illustrating an example of a daily template relating to an activity amount.

FIG. 22 is a waveform chart used for describing processing of forming a seating rate waveform.

MODE FOR CARRYING OUT THE INVENTION

Embodiments and the like of the present technology will be described below with reference to the drawings. Note that the description will be made in the order below.
<1. First Embodiment>
<2. Second Embodiment>
<3. Modified Example>

The embodiments and the like described below are preferred specific examples of the present technology, and the content of the present technology is not limited to these embodiments and the like.

1. First Embodiment

"System Configuration"

Figure 1:
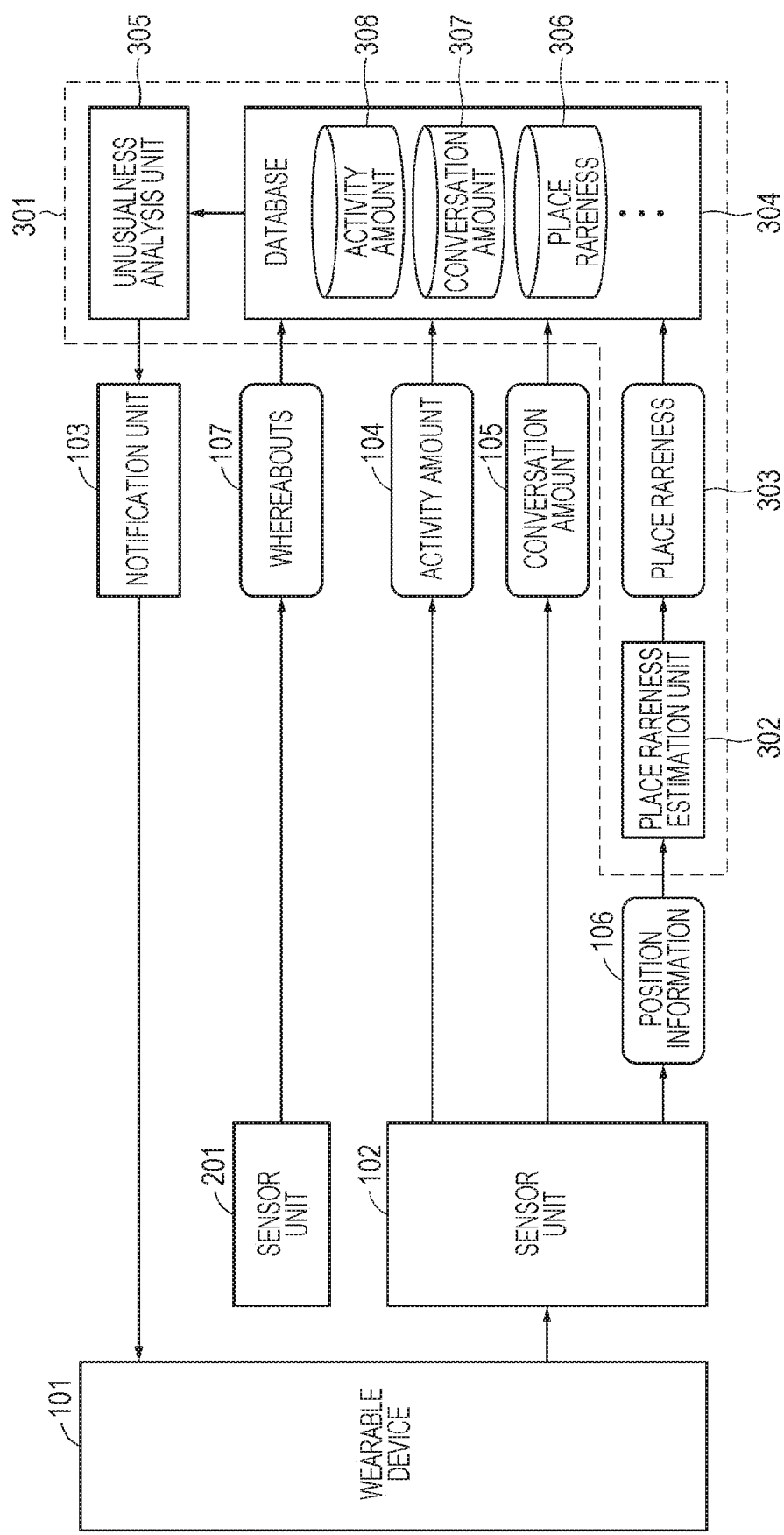
FIG. 1 is a block diagram illustrating an entire system of an information processing apparatus according to the present technology.

FIG. 1 is a block diagram illustrating an entire system of a first embodiment of an information processing apparatus according to the present technology. A wearable device 101 is worn by a user. Specifically, the wearable device 101 is in the form of a wristband, an earphone, a pair of glasses, or the like. Note that the user is an example of objects, and the objects include persons, robots, animals, and the like. The animals include pets and the like.

The wearable device 101 includes a sensor unit 102 as a detection data acquisition unit, and also includes a notification unit 103 that uses wireless communication to perform communication. The notification unit 103 performs wireless communication on the basis of a standard such as Bluetooth (registered trademark), near field communication (NFC), or Wi-Fi (registered trademark) (hereinafter referred to as "wifi", omitting the indication of registered trademark) to avoid complication). Moreover, the wearable device 101 includes a control microcomputer, a battery, a display device, an audio device, and the like. Note that the sensor unit 102 and/or the notification unit 103 may be configured separately from the wearable device 101, for example, in a smartphone.

The sensor unit 102 includes a position sensor that detects user's position information, a motion sensor that detects user's motion or state, a biological information sensor that detects user's biological information, or other sensors. The position sensor can use information of, for example, the global positioning system (GPS), radio frequency identification (RFID), a wifi access point, a wireless base station, or the like. These types of information can be used to detect, for example, latitude and longitude of a current location. Detection data is acquired by the sensor unit 102.

Furthermore, as the motion sensor, for example, a 3-axis acceleration sensor (including an acceleration sensor, a gravity detection sensor, a fall detection sensor, and the like), a 3-axis gyro sensor (including an angular velocity sensor, a camera shake correction sensor, a geomagnetic sensor, and the like), and the like are used. Moreover, the biological information sensor detects a user's pulse (heartbeat), body temperature, sweating, and the like. Moreover, a sensor such as a microphone is provided for the sensor unit 102 to detect a user's conversation. Signal processing is performed so as to extract only conversations from audio signals detected by the microphone. The sensor unit 102 can obtain detection data such as activity amount data 104, conversation amount data 105, and position information 106.

Moreover, a sensor unit 201 as a detection data acquisition unit, and an unusualness detection processing unit 301 are provided. The sensor unit 201 is a fixed sensor such as a human sensor or a camera device mounted on a stationary agent. Note that the sensor unit 201 is not limited to a fixed sensor, and may be a movable sensor. The sensor unit 201 obtains detection data, for example, information indicating whether or not a person is at a certain place (appropriately referred to as whereabouts data) 107.

The activity amount data 104, the conversation amount data 105, and the whereabouts data 107 obtained by the sensor unit 102 and the sensor unit 201 are supplied to the unusualness detection processing unit 301. The position information 106 is supplied to a place rareness estimation unit 302 of the unusualness detection processing unit 301 to form place rareness data 303. The unusualness detection processing unit 301 includes a database 304 and an unusualness analysis unit 305.

The database 304 includes, for example, a place rareness database 306, a conversation amount database 307, an activity amount database 308 that are unique to a user, and the like. The unusualness analysis unit 305 references the database 304 to detect unusualness, and notifies the user (wearable device 101) of a detection result through the notification unit 103. The database 304 includes a database where daily waveform data for template creation is accumulated and a database where real-time waveform data is accumulated. Specifically, the unusualness detection processing unit 301 may be a server or a smartphone.

Figure 2:
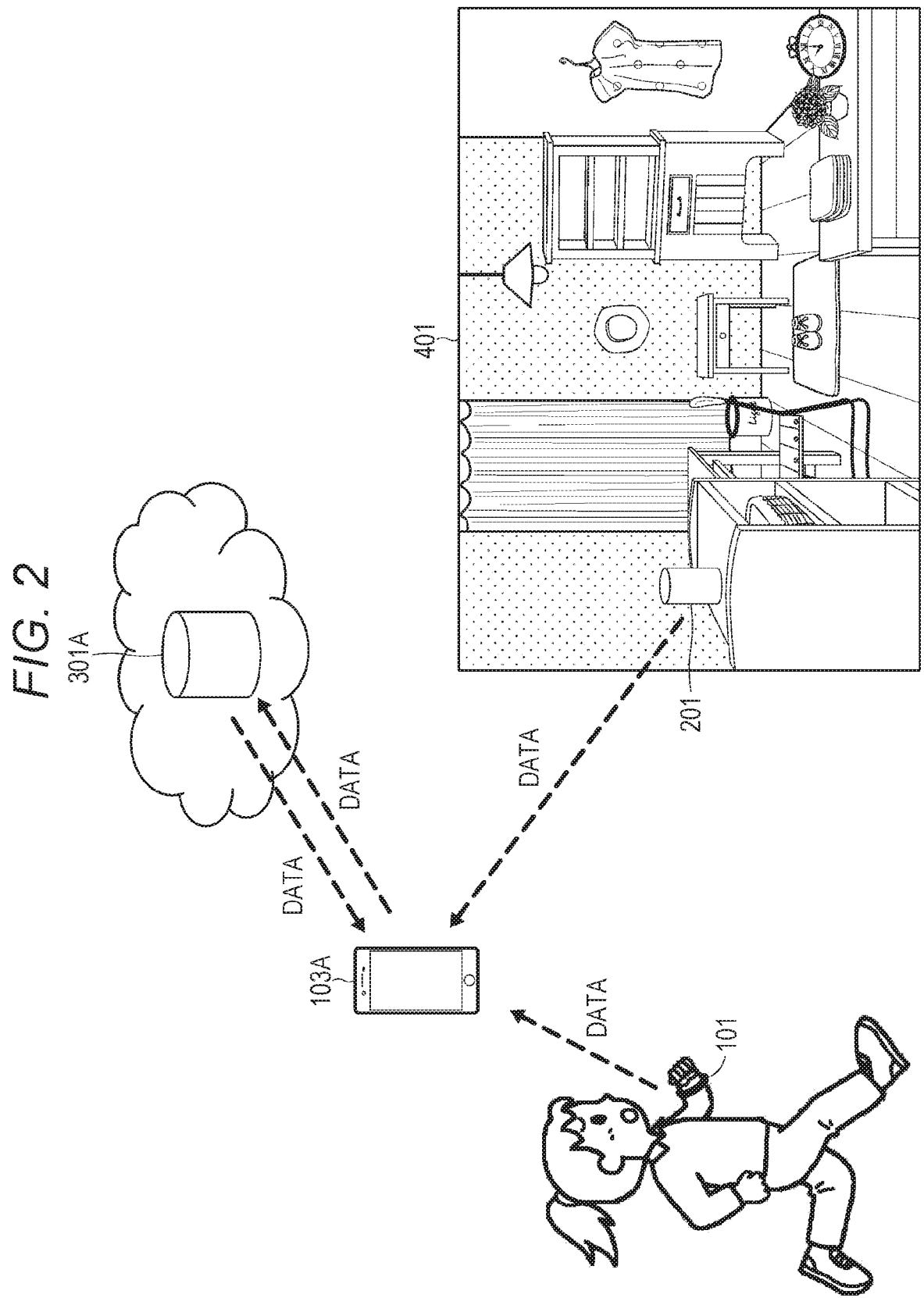
FIG. 2 is a diagram for describing an example of the system of the information processing apparatus according to the present technology.

FIG. 2 is a diagram illustrating an outline of an example of an unusualness detection system. In the example of FIG. 2, a smartphone 103A is used as the notification unit 103. A user wears the wearable device 101 and carries the smartphone 103A. As the unusualness detection processing unit 301, a server 301A is used, to and from which a smartphone 101A can send and receive data.

The fixed sensor unit 201 is installed in a room 401 in a house where the user lives. The sensor unit 201 detects whether or not the user is in the room 401, and whereabouts data based on the detection is transmitted to the server 301A via the smartphone 103A. The sensor unit 201 can detect, not only information indicating whether or not the user is in the room, but also whether or not the user is seated at a desk.

Activity amount data, conversation amount data, and position information obtained by the sensor unit 102 of the wearable device 101 are transmitted to the server 301A through the smartphone 103A. The server 301A includes an unusualness analysis unit and a database. As a result of the analysis, a notification to the user is generated and sent from the server 301A to the smartphone 103A.

Figure 3:
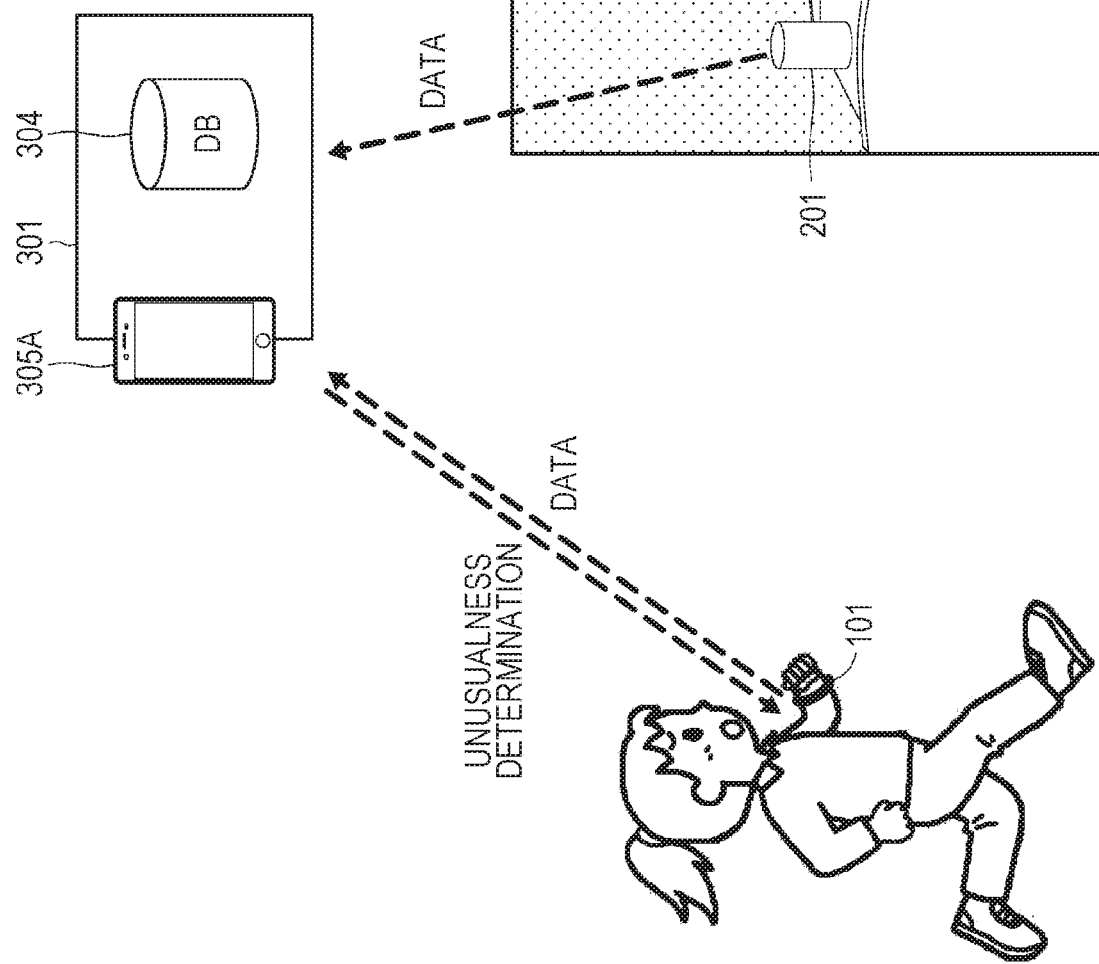
FIG. 3 is a diagram for describing another example of the system of the information processing apparatus according to the present technology.

FIG. 3 is a diagram illustrating an outline of another example of the unusualness detection system. In the example of FIG. 3, a communication unit in the wearable device 101 is used as the notification unit 103. A smartphone 305A and the database 304 are used as the unusualness detection processing unit 301. A smartphone 306A has a communication function.

Activity amount data, conversation amount data, and position information obtained by the sensor unit 102 of the wearable device 101 are sent from the wearable device 101 to the smartphone 305A. Data from the sensor unit 201 is also transmitted to the smartphone 305A. An application installed on the smartphone 305A references the database 304 to perform unusualness detection processing. A notification of a result of the unusualness detection processing is sent to the smartphone 305A or the wearable device 101. The user can thus be informed of the notification.

A table illustrated in FIG. 4 specifically indicates relationships among use cases (detection data), devices, and sensors. The relationships are described below from the top. Note that the order of indication will be "Use case"—"Device"—"Sensor"—"Remarks" in the description.

"Place rareness"—"Wearable device/smartphone"—"GPS/wifi"

"Activity amount"—"Wearable device/smartphone"—"Acceleration sensor, pulse (heartbeat) sensor"

"Conversation amount"—"Wearable device/smartphone"—"Microphone"

"Whereabouts (whether or not a user is at a certain place)"—"Stationary sensor"—"Human sensor/camera"—"The stationary sensor is assumed to be a home agent or the like." Note that not only a stationary sensor but also a movable sensor may be used.

"Change in robot behavior"—"Robot"—"[Amount of contact] tactile sensor/camera, [Conversation amount] microphone)"—"The amount of contact with the robot can also be determined by position information indicating whether a person is nearby."

"Real-time friendliness for each companion"—"Wearable device/smartphone"—"[Companion] GPS/wifi, [Conversation amount] microphone)"—"Position information is used to perform companion determination."

"Exciting place determination"—"Wearable device/smartphone"—"[Place rareness] GPS/wifi, [Excitement degree] pulse (heartbeat) sensor"

"Place rareness"

Processing of the place rareness estimation unit 302 will be described with reference to FIGS. 5A, 5B, and 5C. For example, a maps application can be installed on a smartphone in advance so that a function of this application can be used to detect and save a change in the place the user is staying, that is, a trajectory of movement. FIG. 5A illustrates a time series change in the place the user is staying in the form of a table.

The staying place is recorded every 30 minutes for each date. A place ID is given to each staying place in advance. For example, a place ID "1" is assigned to the user's home, a place ID "2" is assigned to the user's company (workplace), and a place ID "3" is assigned to a station building. When the user is traveling, "x" is assigned.

Rareness of each staying place is calculated from data in the table in FIG. 5A. For each date, each place indicated by a place ID is assigned with "1" if the user has stayed at the place at least once, or "0" if the user has not stayed at the place at all, and a table in FIG. 5B is thus created. Then, place rareness represented by the following formula is calculated.

Staying place rareness=Total number of days recorded/The number of days user has ever stayed The higher the value of the staying place rareness, the rarer the place. For example, in the case of the home, the number of days in which the user has ever stayed is the largest, and the staying place rareness is the lowest. A table in FIG. 5C can be obtained by replacing each place ID in the table in FIG. 5A with the staying place rareness corresponding to the place ID. Passage of time in each date in this table is taken as an x-axis and the staying place rareness is taken as a y-axis to obtain a one-day timeline (time series) of the staying place rareness (hereinafter appropriately referred to as a waveform). This timeline is saved on a memory of the unusualness detection processing unit 301.

In a case where the table in FIG. 5C indicates data of four days, for example, from Jun. 15 to Jun. 18, 2017, the waveform of each date is as illustrated in FIG. 6. FIGS. 5A, 5B, and 5C illustrate, as an example, data of every 30 minutes from 7:00 to 14:30, but a waveform for one day (24 hours) is obtained. Then, a similarity such as a dynamic time warping (DTW) distance between a waveform of a certain day and each of the waveforms of all the dates accumulated is obtained. DTW distances between waveforms of dates in FIG. 6 (between the waveform of Jun. 15, 2017 and each of the waveforms of other days (Jun. 16, 2017, Jun. 17, 2017, and Jun. 18, 2017) are calculated. In the case of the same day, the DTW distance naturally becomes 0. In the case of the date with a low similarity (Jun. 17, 2017), the DTW distance becomes longer. In the case of the date with a high similarity (Jun. 16, 2017), the DTW distance becomes shorter. In this way, the DTW distances are obtained by a brute force comparison, and are represented in the form of a DTW table, in which each date is assigned to one row and one column. Each row in the DTW table represents a feature vector of each date used as the input of clustering.

"DTW Distance"

In one embodiment of the present technology, template matching processing is performed in the unusualness detection processing. Templates are obtained by clustering processing from data in which waveforms as described above are accumulated. In clustering and template matching, a similarity between waveforms is determined. A dynamic time warping method (DTW) is used for comparison. The DTW enables comparison between pieces of time series data that differ in length.

Figure 7:
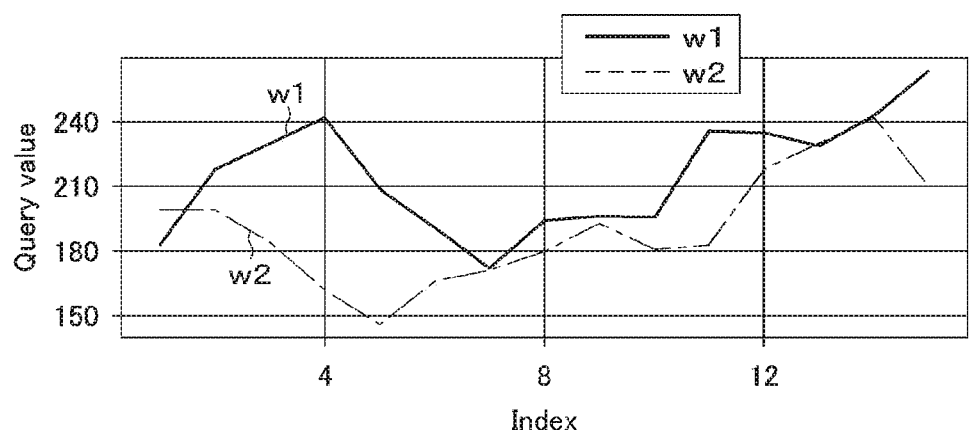
FIG. 7 is a waveform chart used for describing processing of obtaining a DTW distance.

To make a comparison between two waveforms W1 and W2 that differ in length of a time axis as illustrated in FIG. 7, optimum points are compared with each other. That is, the following procedure is used to make a brute force comparison of all the distances between each two points in time series, and find the shortest path (DTW distance).

Step 1: Sequentially compare points from the two waveforms W1 and W2, each pair of the points being connected by a broken line.

Step 2: Calculate a distance (cost) between each two points compared, and create a distance matrix. The distance matrix is expressed by the following formula.

[Mathematical Formula 1]

$$\text{Distance matrix } D = \begin{pmatrix} |x_1 - y_1| & |x_2 - y_1| & \cdots & |x_T - y_1| \\ |x_1 - y_2| & |x_2 - y_2| & \cdots & |x_T - y_2| \\ \vdots & \vdots & \ddots & \vdots \\ |x_1 - y_T| & |x_2 - y_T| & \cdots & |x_T - y_T| \end{pmatrix} \quad (1)$$

Step 3: As shown in the following formula, the minimal value obtained by adding cells of the distance matrix up to step 2 and the distance (cost) between the two points calculated in step 2 becomes the DTW distance at that point of time. (A path that has a minimal sum of distances (costs) between two points up to that point of time is automatically found.)

Step 4: When the cell at the upper right of the distance matrix is reached, the value of that cell is the DTW distance between the time series.

[Mathematical Formula 2]

$$DTW(x, y) = \min \sum_{k}^{k} \left| x_{w_k^x} - y_{w_k^y} \right| \quad (2)$$

"K-means clustering"

In the embodiment of the present technology, k-means clustering is used as a clustering algorithm. An average of clusters is used to classify data into given k clusters. For the number of clusters k, an optimum value is obtained in advance by using the average value. A k-means clustering algorithm will be described with reference to FIGS. 8A, 8B, and 8C.

Step 11: Randomly assign a cluster to each point (DTW distance described above) (FIG. 8A).

Step 12: Calculate centers of gravity (average values of coordinates) of clusters (x in FIGS. 8B and 8C indicates a center of gravity).

Step 13: Calculate a distance between each point and a center of gravity, and assign each cluster to the closest center of gravity instead of the point (FIG. 8C).

Step 14: If no change occurs, the processing ends. As long as a change occurs, the processing returns to step 12, and the processing is repeated. Note that a threshold may be set in advance so that the processing ends if the change is smaller than the threshold.

As a result of such clustering, a daily template is created by using a cluster having the largest number of elements. Data closest to the center of gravity of the cluster is used as the template. After the template has been created, template matching is performed to detect unusualness. The created template is a daily template. The simplified term "template" is also used to mean a daily template.

In template matching, a DTW distance between an input waveform and a daily template is calculated, and the DTW distance at this time is compared with a threshold to detect unusualness.

The unusualness detection processing of the first embodiment will be described below. A default value is used at a stage before a template is created. An example of setting the default value will be described.

In a case of place rareness, places are categorized and a default place rareness is set for each category. Some templates corresponding to user's basic information (gender, age, occupation, and the like) are prepared, and a template that suits the user is set as a default. Examples of the place rareness include "1" for home, "2" for a workplace, "20" for a department store, "60" for a movie theater, and the like.

In a case of an activity amount, user's basal metabolism is set as a default value.

In a case of determining whether or not a user is at a certain place in a room, some templates corresponding to user's basic information (gender, age, occupation, and the like) are prepared, and a template that suits the user is set as a default value. Alternatively, the user themselves manually sets a place (places a stationary sensor) and a time period of detection.

In a case of an amount of conversation, some templates corresponding to user's basic information (gender, age, occupation, and the like) are prepared, and a template that suits the user is set as a default.

Figure 9:
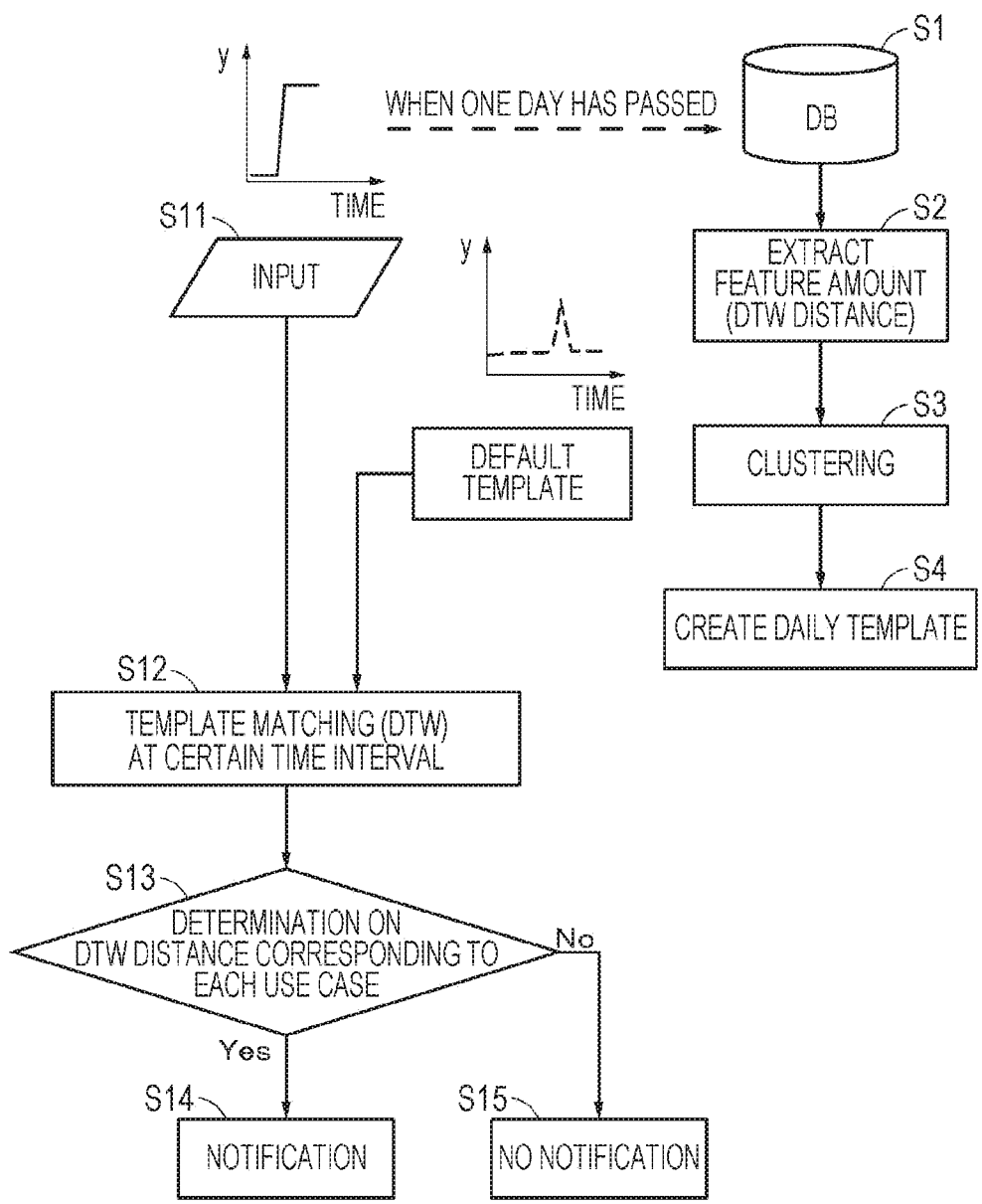
FIG. 9 is a flowchart used for describing unusualness detection processing at a stage before a template is created.

Processing of creating a template will be described with reference to a flowchart in FIG. 9.

For example, a y-axis value (value of detection data) is updated at a certain time interval in a day.

Step S1: When one day has passed, a waveform of the day is stored in a database.

Step S2: A feature amount is extracted from detection data stored in the database. For example, a DTW distance as described above is calculated.

Step S3: The k-means clustering described above is used to perform clustering on the basis of the DTW distance.

Step S4: A daily template is created on the basis of a result of the clustering.

Before the template is created, a default value (default template) is used to perform unusualness detection processing.

Step S11: A y-axis value is input from a sensor associated with the user.

Step S12: The degree of matching with the default template is calculated at a certain time interval. It is determined that the smaller the DTW distance, the higher the degree of matching.

Step S13: A determination on the DTW distance is made corresponding to each use case. For example, the DTW distance is compared with a threshold.

Step S14: If the DTW distance is larger than the threshold, a notification of detection of unusualness is given.

Step S15: If the DTW distance is smaller than the threshold, no notification is given.

Figure 10:
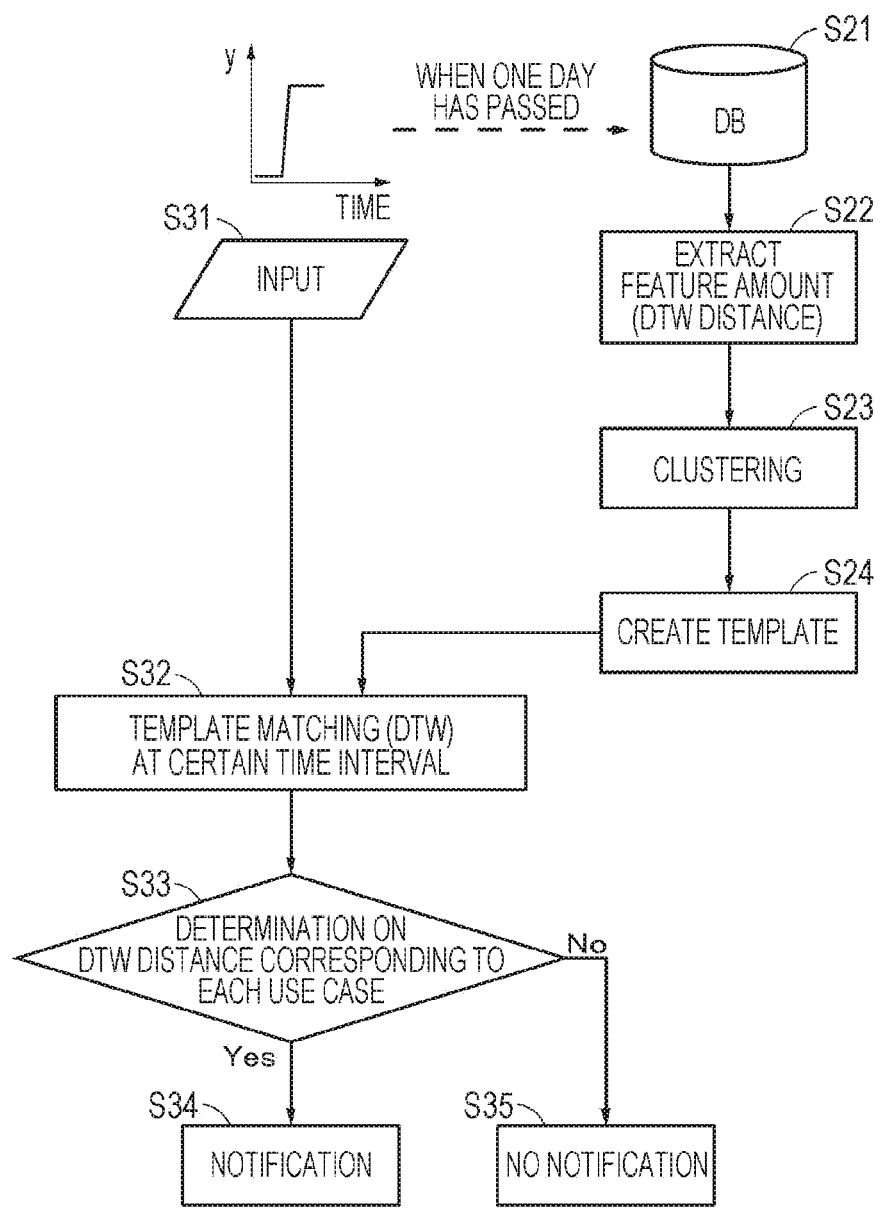
FIG. 10 is a flowchart used for describing unusualness detection processing at a stage after a template has been created.

Processing after a template has been created (a state where user data has been accumulated to some extent) will be described with reference to FIG. 10. Template creation processing and unusualness detection processing are performed in parallel. The template creation processing is constantly performed to create an updated template. The template creation processing includes, as in the one described above, step S21 (creating a database), step S22 (extracting a feature amount (DTW distance), step S23 (clustering), and step S24 (creating a template).

The unusualness detection processing includes, as in the one described above, step S31 (inputting a y-axis value), step S32 (template matching at a certain time interval), and step S33 (determination on the DTW distance corresponding to each use case). In accordance with a result of the determination in step S33, a notification is given (step S34) or no notification is given (step S35). In step S32, the template created by the template creation processing is used. In the template matching in step S12 and step S32, two waveforms are compared, and the DTW distance (similarity between two waveforms) can be calculated even in a case where the input waveform and the template differ in time width. In the determination processing in step S13 and step S33, a threshold is set, and if the DTW distance exceeds the threshold, the matching result is No (a notification of this determination result is given).

Figure 11A:
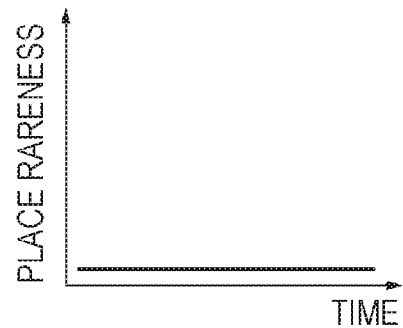
FIGS. 11A, 11B, 11C, and 11D are waveform charts illustrating specific examples of a place rareness waveform.
Figure 11B:
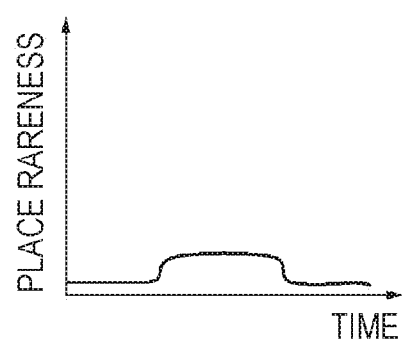
Figure 11C:
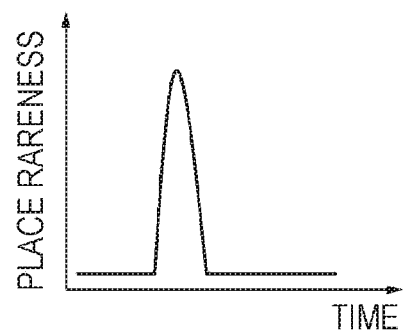
Figure 11D:
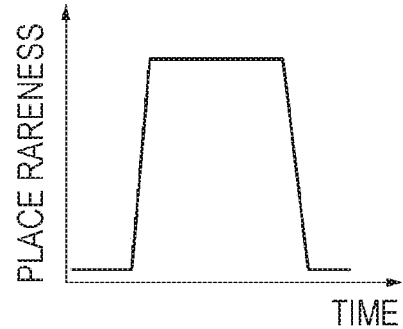

FIGS. 11A, 11B, 11C, and 11D illustrate an example of a daily waveform. The y-axis indicates place rareness. The place rareness value is lowest in a case where the user is at home. FIG. 11B illustrates a waveform in a case where, for example, the user has left for work, worked at the company, and then returned home. FIG. 11A illustrates a waveform in a case where the user has stayed at home throughout the day. FIG. 11C illustrates a waveform in a case where the user has visited a place that the user does not usually go, such as a movie theater or a theater, for example, during a certain period of time in a day. FIG. 11D illustrates a waveform in a case where the user has gone on a trip, for example. The place rareness shows a high value during most hours of the day.

FIG. 12 illustrates an example of a daily template in a case where the place rareness is shown on the y-axis. A feature amount is obtained from an input waveform, four clusters are formed by clustering processing, and a typical waveform of one cluster (daily cluster) having the largest number of elements is set as a daily template. The clusters are referred to as cluster 1, cluster 2, cluster 3, and cluster 4. An example of the number of days (the number of days applicable) in which the DTW distance between an actual waveform and each daily template is small is illustrated. Note that the number of days applicable means the number of elements in a cluster.

Cluster 1 represents a case where the value of the place rareness remains low throughout the day, and is characterized in that the user has been in a familiar place such as home or the workplace throughout the day. Cluster 1 has the largest number of days applicable.

Cluster 2 represents a case where the value of the place rareness is high during a short time period, and is characterized in that the user has been in a rare place for a short time (for example, a case where the user has visited a nearby place). Cluster 2 has the second largest number of days applicable.

Cluster 3 represents a case where the value of the place rareness is high during a long time period, and is characterized in that the user has been in a rare place for a long time (for example, a case where the user has visited a faraway place). Cluster 3 has the third largest number of days applicable.

Cluster 4 represents a case where the value of the place rareness is high almost throughout the day, and is characterized in that the user has been in a rare place throughout the day (for example, a case where the user has been on a trip). Cluster 4 has the fewest number of days applicable. A daily template is created using cluster 1, which has the largest number of elements.

"Notifications"

Examples of a notification method for giving a notification of a template matching result includes a pop-up notification in which the content of the notification is displayed as characters or images. Unusual events that can be detected are classified into negative unusual events and positive unusual events on a use-case basis, and a different notification timing is set for each of them. A notification by voice, vibration, an icon, or the like other than a pop-up notification may be used, for example.

Figure 13A:
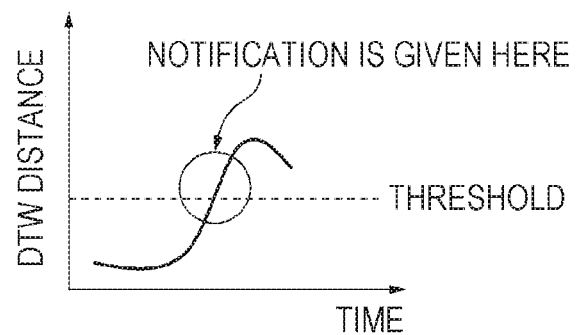
FIGS. 13A and 13B are diagrams used for describing a timing of notification.

In a case where a negative unusual event is detected, a notification is given if both of the following conditions are satisfied: an average value of the y-axis is lower than an average value of the template; and a relationship of "DTW distance>threshold" is established (FIG. 13A). In this case, for early detection of an unusual event (anything extraordinary), a notification is given immediately if there is anything that is different from usual. Specific examples include a case where the y-axis indicates an activity amount, which is used to monitor an elderly person or a pet, a case where the y-axis indicates a conversation amount, which is used to visualize fatigue or determine a health problem, and a case where the y-axis indicates whether or not a user is at a certain place, which is used to discipline a child.

Figure 13B:
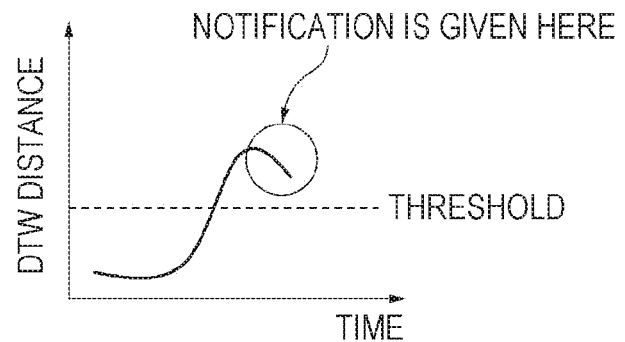

In a case where a positive unusual event is detected, a notification is given if both of the following conditions are satisfied: a relationship of "DTW distance>threshold" is established; and the DTW distance shows a maximal value or has just shown the maximal value (FIG. 13B). That is, a notification is given when the unusualness has peaked out and the user has calmed down. Specific examples include a case where the y-axis indicates place rareness, which is used to suggest posting on SNS, and a case where the y-axis indicates an activity amount, which is used to praise an increase in the activity amount.

"Example of Use Case Where Y-Axis Indicates Position (Place Rareness)"

Figure 14:
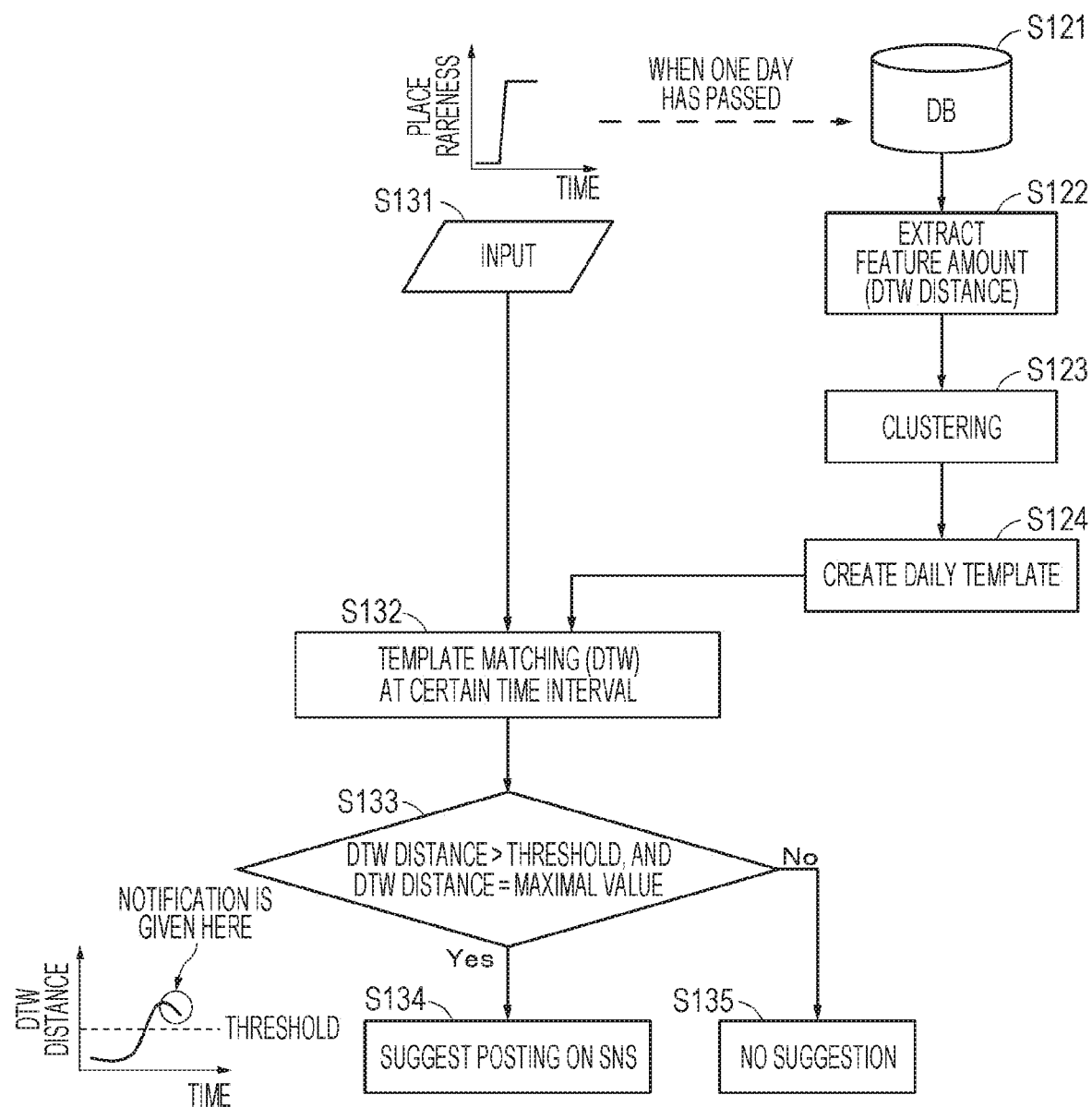
FIG. 14 is a flowchart for describing unusualness detection processing in a case where detection data is place rareness.

FIG. 14 is a flowchart illustrating unusualness detection processing in a case where the y-axis indicates a position (place rareness). Processing after a template has been created is illustrated. Template creation processing and unusualness detection processing are performed in parallel. The template creation processing is constantly performed to create an updated template. The template creation processing includes, as in the one described above, step S121 (creating a database), step S122 (extracting a feature amount (DTW distance), step S123 (clustering), and step S124 (creating a template). In this use case example, unusualness is determined in real-time on the basis of a place where a user is staying to suggest posting on SNS.

The unusualness detection processing includes, as in the one described above, step S131 (inputting a y-axis value), step S132 (template matching at a certain time interval), and step S133 (determination on the DTW distance). In accordance with a result of the determination in step S133, a notification is given (step S134) or no notification is given (step S135). In step S132, the daily template created by the template creation processing is used.

Figure 15A:
FIGS. 15A, 15B, 15C, and 15D are diagrams illustrating an example of a notification given to a user.

In the template matching in step S132, a DTW distance between an input y value and the daily template created in step S124 is calculated at a certain time interval. It is determined that the smaller the DTW distance, the higher the degree of matching. In the determination processing in step S133, for example, DTW distances from four clusters as illustrated in FIG. 12 are calculated, and a cluster with the smallest DTW distance is determined. If (DTW distance>threshold) and (DTW distance=maximal value) are both satisfied, a notification (suggestion to post on SNS) is given in step S134. This is a case of a positive unusual event, so a notification is given when the unusualness has peaked out and the user has calmed down. For example, a message such as "Would you like to share records of your unusual experience with your friends?" as illustrated in FIG. 15A is presented to the user.

"Example of use case where y-axis indicates activity amount"

Figure 16:
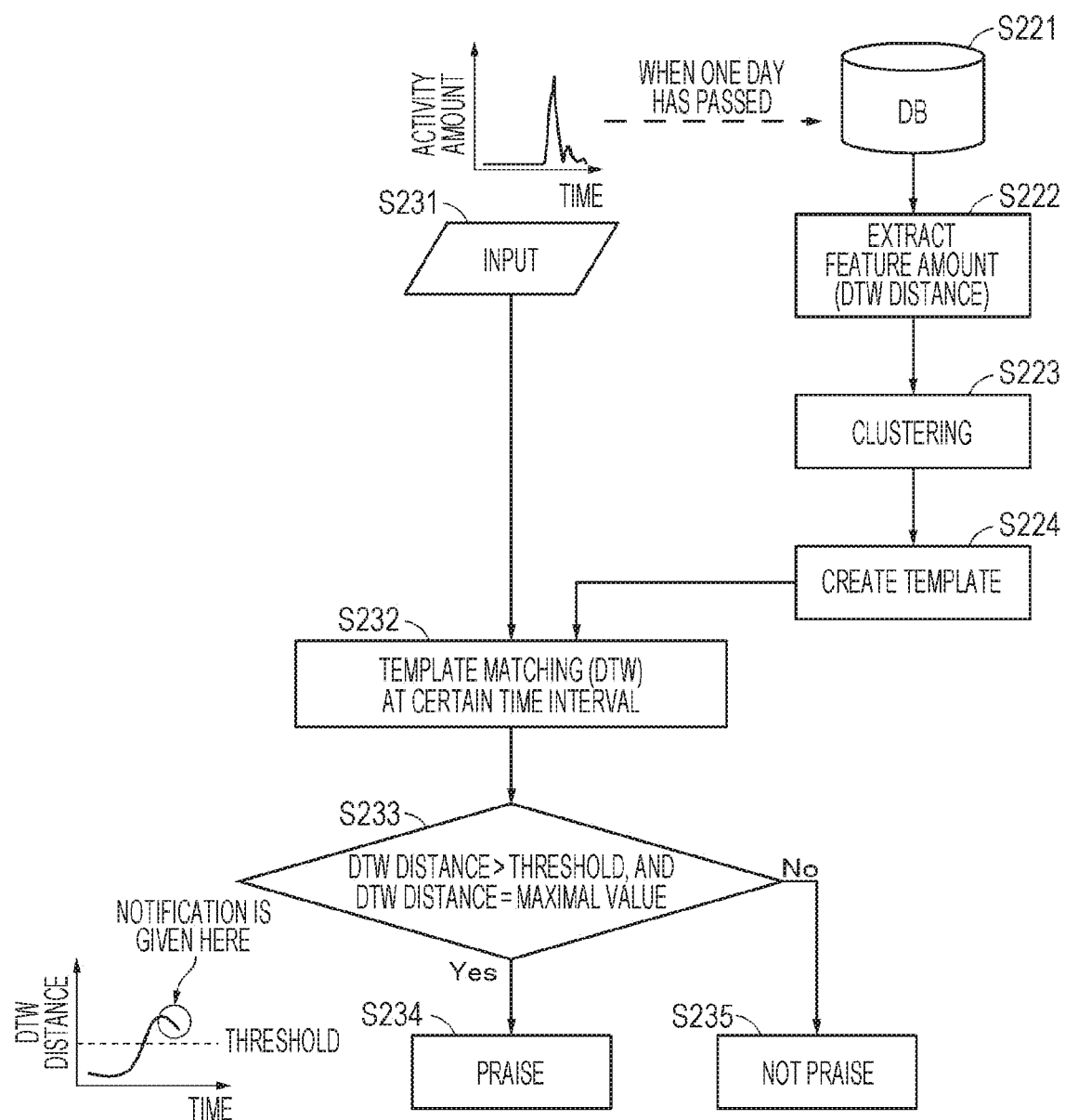
FIG. 16 is a flowchart for describing unusualness detection processing in a case where detection data is an activity amount.

FIG. 16 is a flowchart illustrating unusualness detection processing in a case where the y-axis indicates an activity amount. Processing after a template has been created is illustrated. In this use case example, if a user has taken more exercise than usual, it is detected in real time to praise the user. As a result, an effect of improving motivation of the user is created.

Step S221: A value of the activity amount is updated at a certain time interval in a day. When one day has passed, a waveform of the day is stored in a database. Template creation processing and unusualness detection processing are performed in parallel. The template creation processing is constantly performed to create an updated daily template. The template creation processing includes, as in the one described above, step S221 (creating a database), step S222 (extracting a feature amount (DTW distance), step S223 (clustering), and step S224 (creating a template).

FIG. 17 illustrates an example of a daily template in a case where the activity amount is shown on the y-axis. A feature amount is obtained from an input waveform, three clusters are formed by clustering processing, and a typical waveform (waveform) of each cluster is set as a template. The clusters are referred to as cluster 1, cluster 2, and cluster 3. An example of the number of days (the number of days applicable) in which the DTW distance between an actual waveform and each cluster is small is illustrated.

Cluster 1 represents a case where the value of the activity amount remains low throughout the day, and is characterized in that no vigorous exercise has been performed, for example, commuting to and from work is the only activity that can be called exercise. Cluster 1 has the largest number of days applicable.

Cluster 2 represents a case where the value of the activity amount becomes high after a user has returned home, and is characterized in that the user has been jogging after returning home. Cluster 2 has the second largest number of days applicable.

Cluster 3 represents a case where the activity amount becomes high in a time period during daytime, and is characterized in that the user has been jogging on a holiday. Cluster 3 has the fewest number of days applicable. A daily template is created using cluster 1, which has the largest number of elements.

The unusualness detection processing includes, as in the one described above, step S231 (inputting a y-axis value), step S232 (template matching at a certain time interval), and step S233 (determination on the DTW distance). In accordance with a result of the determination in step S233, a notification is given (step S234) or no notification is given (step S235). In the template matching in step S232, the template created by the template creation processing is used.

Figure 15B:

In the template matching in step S232, a DTW distance between an input y value and the daily template created in step S224 is calculated at a certain time interval. It is determined that the smaller the DTW distance, the higher the degree of matching. In the determination processing in step S233, for example, a DTW distance from the template created from cluster 1 illustrated in FIG. 17 is calculated. If (DTW distance>threshold) and (DTW distance=maximal value) are both satisfied, a notification (praise) is given in step S234. This is a case of a positive unusual event, so a notification is given when the unusualness has peaked out and the user has calmed down. For example, a message "Congratulations! You have been more active than usual." as illustrated in FIG. 15B is presented to the user. If the conditions of step S233 are not satisfied, no praise is given (step S235).

In a case where the y-axis indicates an activity amount, there are use case examples other than the example described above. For example, on the basis of a decrease in the activity amount, a fatigue state of the day is visualized and a proposal for taking a rest is made. In this example, the conditions for template matching are changed to (DTW distance>threshold) and (average activity amount<average activity amount of template). If these conditions have been satisfied for about a week in a row, a notification of proposal for taking a rest is given.

Other use case examples where the y-axis indicates an activity amount include monitoring of an elderly person or a pet. That is, an alert is generated if the activity amount becomes lower than usual, or an alert is generated at a time of day when the activity amount usually becomes high (at exercise time) to encourage exercise. In this example, the conditions for template matching are changed to (DTW distance>threshold) and (average activity amount<average activity amount of template). The notification message is changed as appropriate in each example.

Moreover, as another use case example, it is possible to preliminarily extract people who have similar life rhythms from daily templates based on the activity amount so that the extract people can compete against each other on the activity amount in real time. People share their daily templates with others, the daily templates are matched, and about five people with similar life rhythms are automatically extracted. The activity amounts of the extracted people are compared in real time on an individual basis. The conditions for template matching are changed to (DTW distance>threshold) and (activity amount of user>activity amount of extracted person). If the conditions are satisfied for all the extracted people, the user is praised.

"Example of Use Case Where Y-Axis Indicates Conversation Amount"

Figure 18:
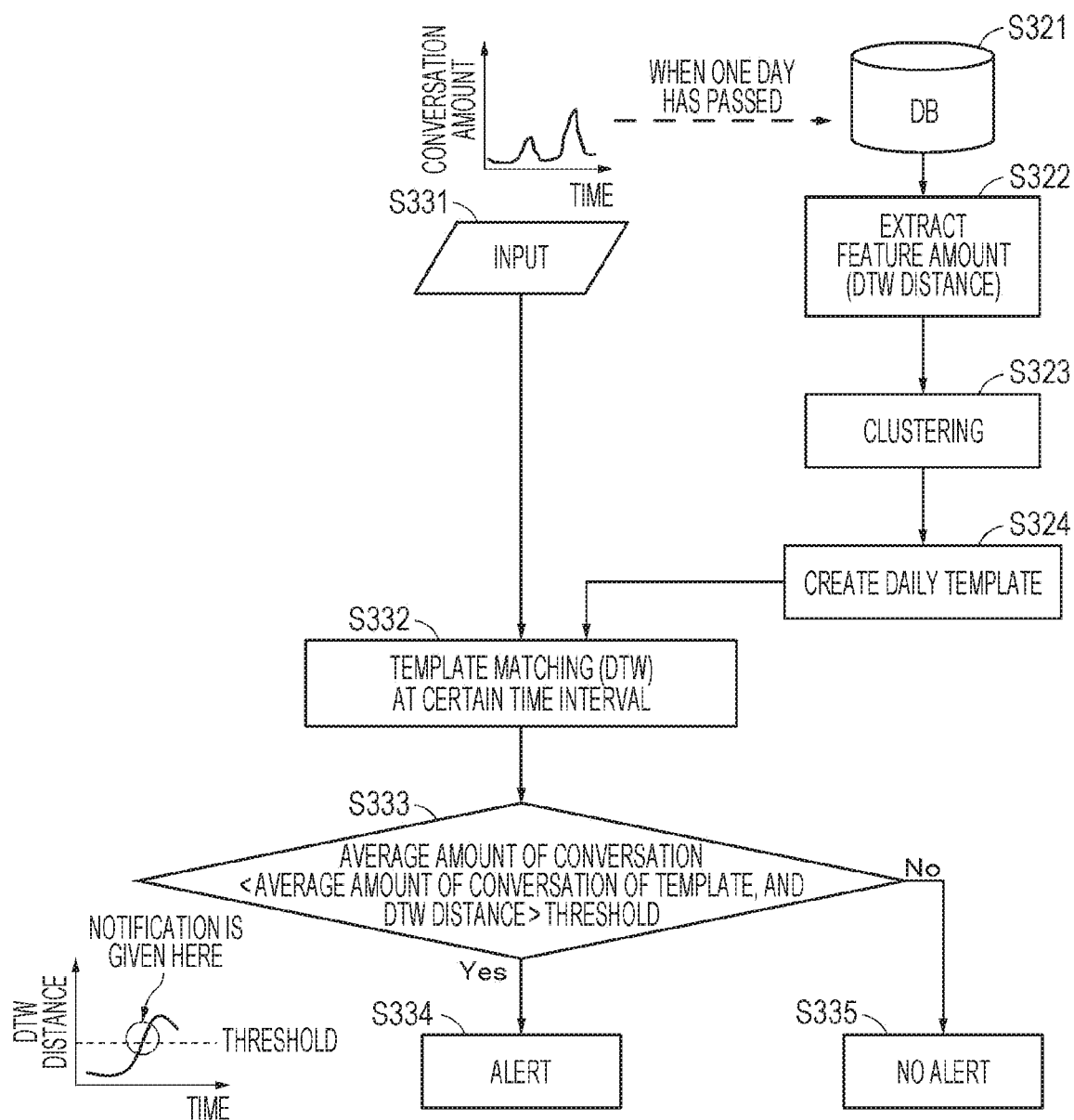
FIG. 18 is a flowchart for describing unusualness detection processing in a case where detection data is a conversation amount.

FIG. 18 is a flowchart illustrating unusualness detection processing in a case where the y-axis indicates an amount of conversation. Processing after a template has been created is illustrated. This use case example aims at early detection of a depression symptom from a decrease in the amount of conversation.

Figure 19:
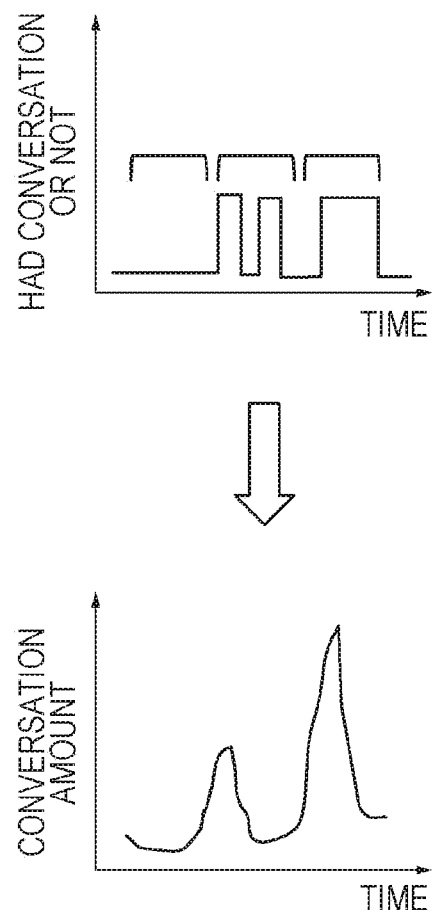
FIG. 19 is a waveform chart used for describing processing of forming a conversation amount waveform.

In step S331, a value of the conversation amount is updated at a certain time interval in a day. When one day has passed, a waveform of the day is stored in a database. FIG. 19 illustrates a definition of an amount of conversation. A waveform is obtained in which a time when a user has had a conversation is set to a high level (for example, the value is 1), and a time when the user has had no conversation is set to a low level (for example, the value is 0). Data regarding whether or not the user has had a conversation during a predetermined period of time, for example, 30 minutes, is accumulated to calculate the amount of conversation during the 30 minutes. The amount of conversation is recorded every 30 minutes with passage of time in one day shown on a horizontal axis, and a waveform of the amount of conversation in one day is thus obtained.

Figure 20A:
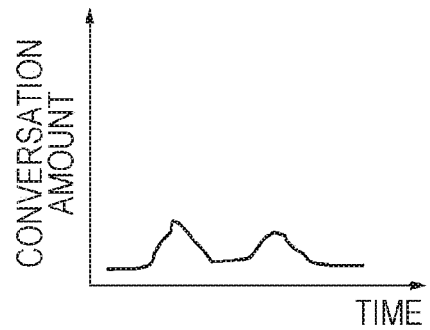
FIGS. 20A, 20B, 20C, and 20D are waveform charts illustrating specific examples of a conversation amount waveform.
Figure 20B:
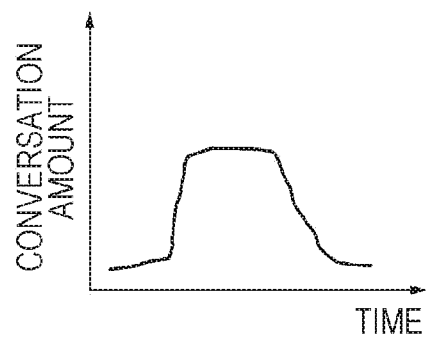
Figure 20C:
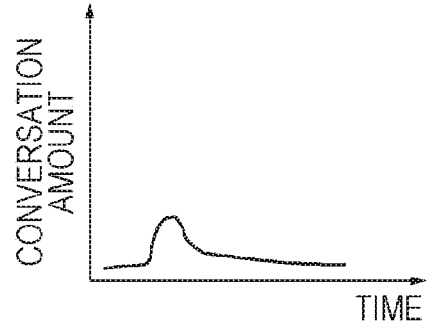
Figure 20D:
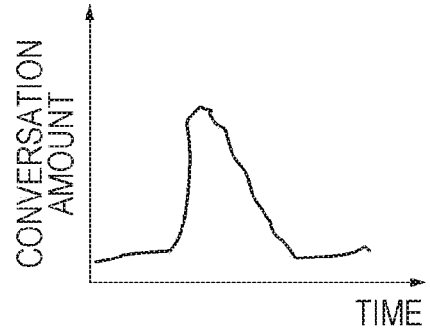

FIGS. 20A, 20B, 20C, and 20D illustrate examples of a waveform of one day in a case where the y-axis indicates an amount of conversation. FIG. 20A illustrates an example in which the amount of conversation increases during a time period each in the morning and in the afternoon, but the amount of conversation is small as a whole. FIG. 20B illustrates an example in which the amount of conversation is large due to a meeting in a company throughout the day. FIG. 20C illustrates a case where the amount of conversation increases during a time period in the morning, but the amount of conversation is small as a whole. FIG. 20D illustrates a waveform in a case where the amount of conversation increases around noon.

Template creation processing and unusualness detection processing are performed in parallel. The template creation processing is constantly performed to create an updated template. The template creation processing includes, as in the one described above, step S321 (creating a database), step S322 (extracting a feature amount (DTW distance), step S323 (clustering), and step S324 (creating a template).

The unusualness detection processing includes, as in the one described above, step S331 (inputting a y-axis value), step S332 (template matching at a certain time interval), and step S333 (determination on the DTW distance). In accordance with a result of the determination in step S333, an alert is made (step S334) or no alert is made (step S335). In the template matching in step S332, the template created by the template creation processing is used.

Figure 15C:

In the template matching in step S332, a DTW distance between an input y value and the daily template created in step S324 is calculated at a certain time interval. It is determined that the smaller the DTW distance, the higher the degree of matching. In the determination processing in step S333, if (average amount of conversation<average amount of conversation of template) and (DTW distance>threshold) are satisfied, an alert is made in step S334. This is a case of a negative unusual event, so an alert is made as soon as the DTW distance exceeds the threshold. For example, a message "You have had less amount of conversation than usual. Let's consciously communicate with others." as illustrated in FIG. 15C is presented to the user. If the conditions of step S333 are not satisfied, no alert is generated (step S335). In the use case described above, a depression symptom can be detected early from a decrease in the amount of conversation.

Other use case examples where the y-axis indicates an amount of conversation include a method of detecting a cold early from a decrease in the amount of conversation. The method can be implemented by performing processing similar to that of early detection of depression described above.

Moreover, as another use case example, an amount of conversation is used to quantify a participation rate in a meeting or a class. The amount of conversation is monitored only during time periods of meetings or classes. Data is accumulated in the database every time a meeting or class ends.

Moreover, as another use case example, a ratio between an input amount and an output amount of conversation is used to visualize a health level. The y-axis indicates an amount of conversation expressed by a ratio of "user's conversation amount (output amount)/other people's conversation amount (input amount)" (which is available by using voice recognition). The conditions for template matching are changed to (DTW distance>threshold) and (average input amount/output amount>average input amount/output amount of template).

Moreover, as another use case example, an amount of conversation of a user is monitored at meetings, drinking parties, and the like, and if the amount of conversation remains small for days on end, an alert is generated to suggest having a conversation (making a remark). The y-axis indicates the ratio between the input amount and the output amount of conversations during a limited time. The conditions for template matching are changed to (DTW distance>threshold) and (average input amount/output amount>average input amount/output amount of template). If these conditions for template matching have been satisfied for about a week in a row, an alert is generated to encourage making a remark.

"Example of Use Case Where Y-Axis Indicates Whether or Not User is at Certain Place in Room"

Figure 21:
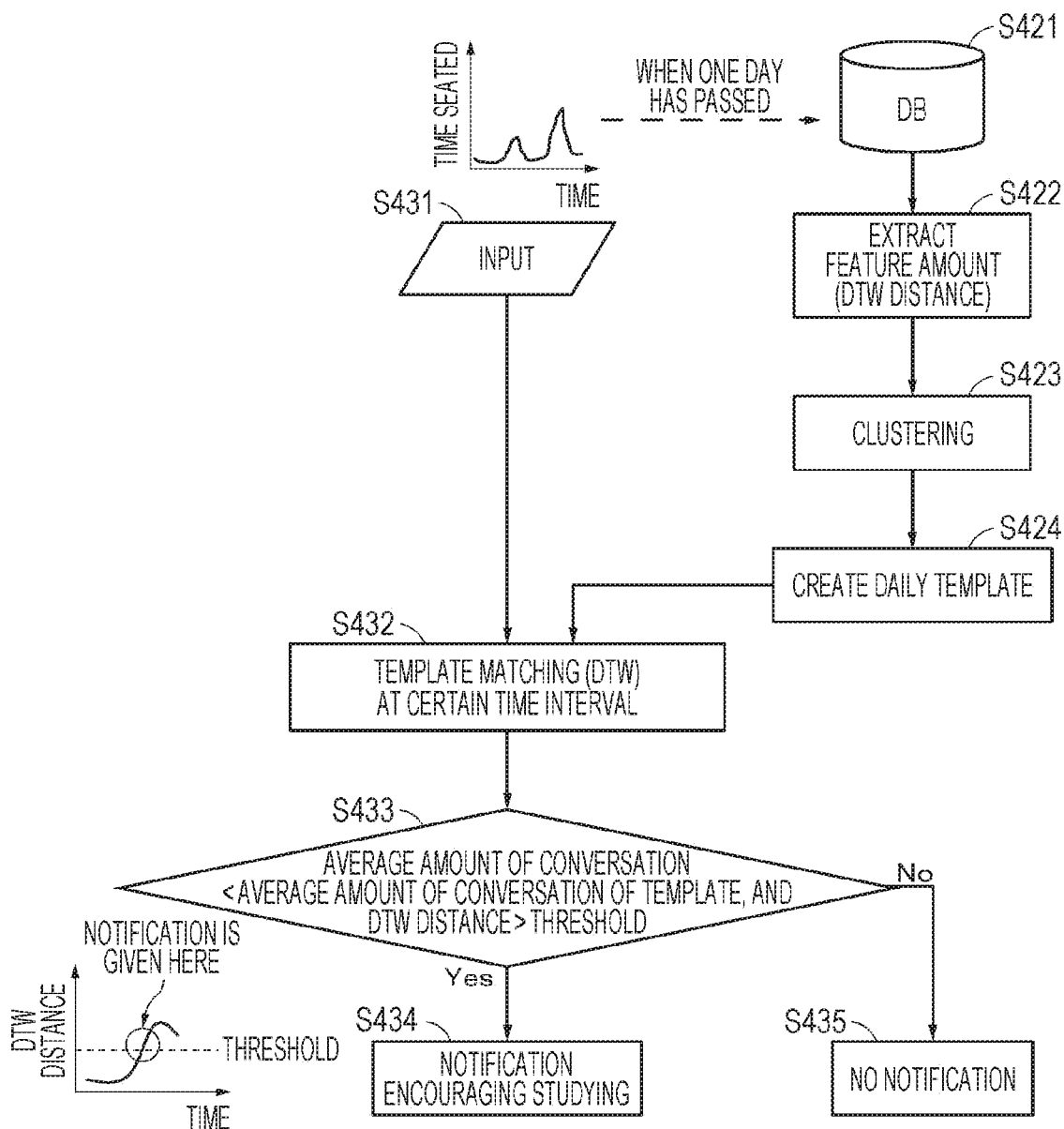
FIG. 21 is a flowchart for describing unusualness detection processing in a case where detection data is a seating rate.

FIG. 21 is a flowchart illustrating unusualness detection processing in a case where the y-axis indicates whether or not a user is at a certain place in a room. As a specific example, determining whether or not a user is at a desk (seated) is used to help the user make a habit of studying. The y-axis indicates a seating rate. Processing after a template has been created is illustrated.

In step S421, a value of the seating rate is updated at a certain time interval in a day. When one day has passed, a waveform of the day is stored in a database. FIG. 22 illustrates a definition of a seating rate. A waveform is obtained in which a time when a user is seated is set to a high level (for example, the value is 1), and a time when the user is not seated is set to a low level (for example, the value is 0). Data regarding whether or not the user is seated during a predetermined period of time, for example, 30 minutes, is accumulated to calculate the seating rate during the 30 minutes. The seating rate is recorded every 30 minutes with passage of time in one day shown on a horizontal axis, and a waveform of the seating rate in one day is thus obtained.

Figure 23A:
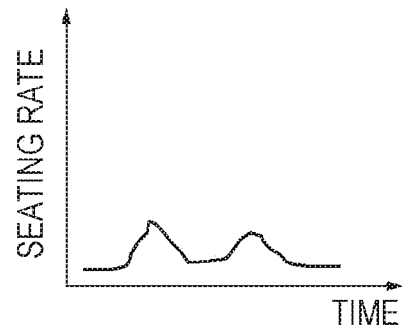
FIGS. 23A, 23B, 23C, and 23D are waveform charts illustrating specific examples of a seating rate waveform.
Figure 23B:
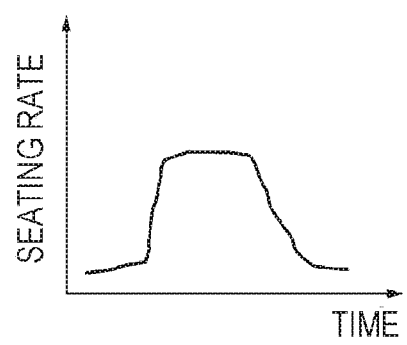
Figure 23C:
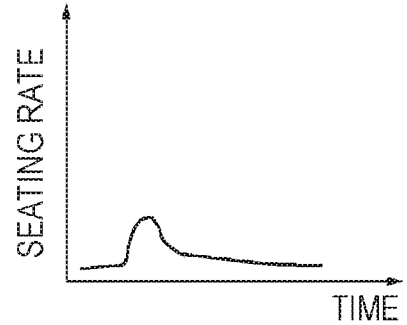
Figure 23D:
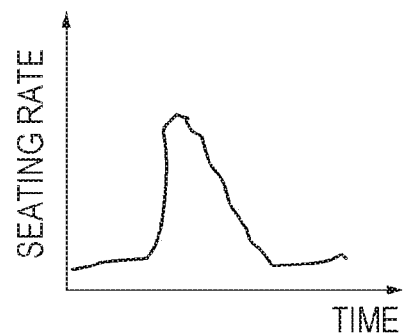

FIGS. 23A, 23B, 23C, and 23D illustrate examples of a waveform of one day in a case where the y-axis indicates a seating rate. FIG. 23A illustrates a waveform in a case where the user has been seated for a relatively short time in the morning and in the afternoon. FIG. 23B illustrates a case where the seating rate is high throughout the day. FIG. 23C illustrates a case where the user has been seated in the morning, but has not been seated during other times. FIG. 23D illustrates a waveform in a case where the seating rate is high from around noon to the evening.

Template creation processing and unusualness detection processing are performed in parallel. The template creation processing is constantly performed to create an updated template. The template creation processing includes, as in the one described above, step S421 (creating a database), step S422 (extracting a feature amount (DTW distance), step S423 (clustering), and step S424 (creating a template).

The unusualness detection processing includes, as in the one described above, step S431 (inputting a y-axis value), step S432 (template matching at a certain time interval), and step S433 (determination on the DTW distance). In accordance with a result of the determination in step S433, a notification is given (step S434) or no notification is given (step S435). In the template matching in step S432, the template created by the template creation processing is used.

Figure 15D:

In the template matching in step S432, a DTW distance between an input y value and the daily template created in step S424 is calculated at a certain time interval. It is determined that the smaller the DTW distance, the higher the degree of matching. In the determination processing in step S433, if (average seating rate<average seating rate of template) and (DTW distance>threshold) are satisfied, a notification is given in step S434. The notification is a message encouraging studying. For example, a notification message "Your study time is less than usual. Let's make a habit of studying." as illustrated in FIG. 15D is given. The notification is given at a point of time when the DTW distance exceeds the threshold. This helps make a habit of studying. If the conditions of step S433 are not satisfied, no notification is given.

Other examples of the use case where the y-axis indicates whether or not a user is at a certain place will be described. Determining (whether or not in bed) can be used for self-management of a sleep rhythm. The input waveform has the y-axis indicating "whether or not in bed". A notification encouraging sleep can be given to help manage the sleep rhythm.

Determining (whether or not at the user's desk in the workplace or the like) can be used to diagnose a work efficiency. The y-axis of the input waveform is changed to "whether or not at the user's desk in the workplace or the like".

Determining (whether or not a user has gone over to a shelf) can be used to get a reminder such as "Do you have your commuter pass with you?" not to forget something. The y-axis is changed to "whether or not the user has approached the shelf". The notification is a reminder not to forget something.

Determining (whether or not in a smoking area or the like) can be used to reprove a user if the user has gone to a smoking area, and this helps improve smoking habits. The y-axis is changed to "whether or not in a smoking area" In a similar manner, this can also be applied to undesirable places other than a smoking area.

"Power Saving"

Figure 24:
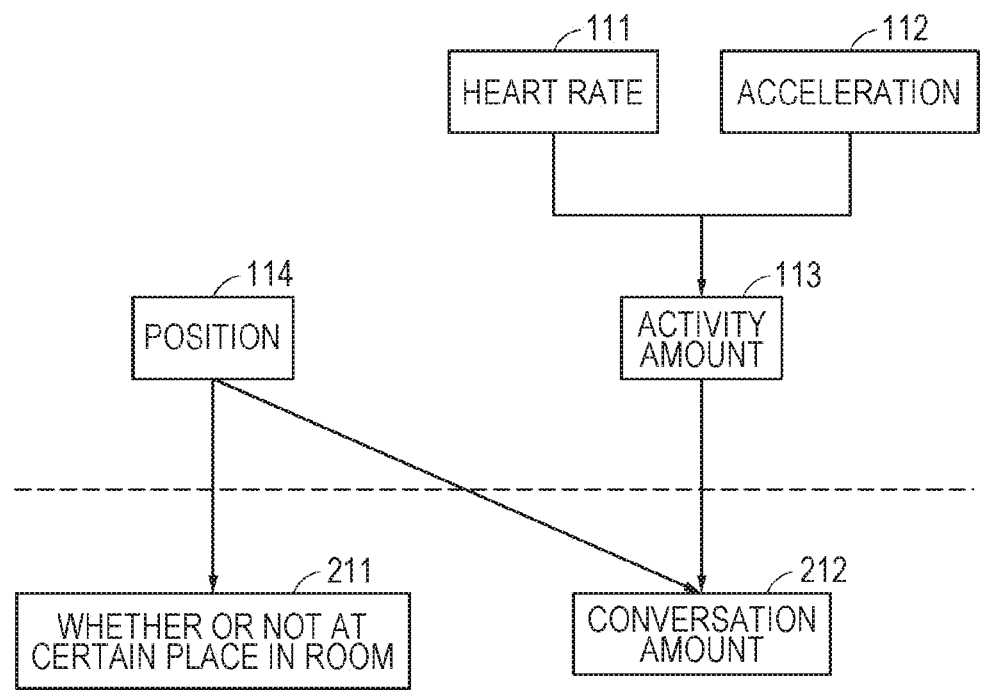
FIG. 24 is a block diagram used for describing a system having a plurality of sensors.

As in a configuration in FIG. 24, in order to obtain data of a plurality of y-axes, for example, a heart rate sensor 111 and an acceleration sensor 112 are used to obtain data of activity amount 113, and a position sensor 114 is used to obtain position information. These sensors 111, 112, and 114 are provided in a wearable device, and their powers are always on.

On the other hand, a sensor 211 for detecting whether or not a user is at a certain place in a room and a conversation amount detecting sensor 212 are provided. The sensor 211 for detecting whether or not a user is at a certain place in a room is required to perform detection when the user is at home or at a workplace, so its power is turned on only when the user is at home or at the workplace on the basis of position information. Furthermore, the conversation amount detecting sensor 212 is required to detect an amount of conversation only when the user is with someone on the basis of position information or when the activity amount is higher than energy consumption at rest. In these cases, the power is turned on. In this way, the power can be turned on only when necessary, and this reduces power consumption.

2. Second Embodiment

"Use of Amount of Contact and Amount of Conversation with Robot Pet"

Figure 25:
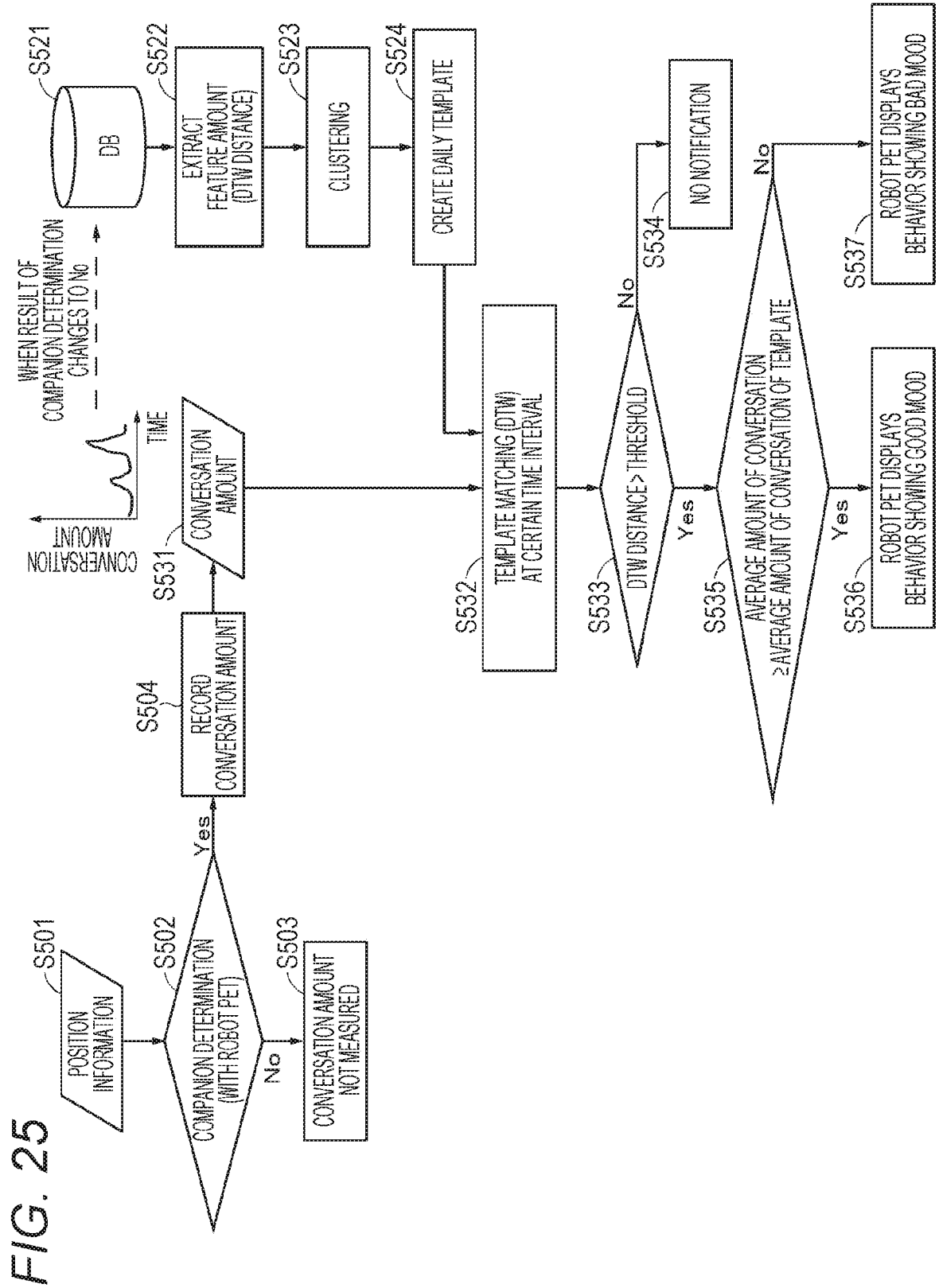
FIG. 25 is a flowchart for describing processing using an amount of contact and an amount of conversation with a robot pet.

A second embodiment is an example of using a plurality of y-axes. A first example of using a plurality of y-axes will be described with reference to a flowchart in FIG. 25.

Step S501: Position information is acquired.

Step S502: Companion determination or amount of contact determination. That is, whether or not a user is with a robot pet is determined. An amount of contact with the robot pet is determined.

Step S503: If it is determined in step S502 that the user is not with the robot pet, the amount of conversation is not measured. In this case, power consumption can be reduced by not turning on power of a sensor for recording the amount of conversation.

Step S504: On the other hand, if it is determined in step S503 that the user is with the robot pet, the amount of conversation is recorded.

Step S521: When the result of the companion determination in step S502 changes to No, a waveform of the amount of conversation is stored in a database.

Step S522: A feature amount is extracted from detection data stored in the database. For example, a DTW distance is calculated.

Step S523: Clustering is performed on the basis of the feature amount.

Step S524: A daily template is created on the basis of a result of the clustering.

Step S531: Input processing is performed. A waveform of the amount of conversation between the user and the robot pet is input.

Step S532: Template matching is performed between the amount of conversation input at a certain time interval and the daily template created in step S524 (a DTW distance is calculated).

Step S533: It is determined whether or not "DTW distance>threshold" is satisfied.

Step S534: If the condition of step S533 is not satisfied, no notification is given.

Step S535: If the condition of step S533 is satisfied, it is determined whether or not "average amount of conversation average amount of conversation of template" is satisfied.

Step S536: If the condition of step S535 is satisfied, the robot pet displays a behavior showing a good mood.

Step S537: If the condition of step S535 is not satisfied, the robot pet displays a behavior showing a bad mood.

In this way, the behavior of the robot pet can be changed in accordance with the amount of conversation with the robot pet. The amount of contact may be detected by the period of time, the number of times, and the like the user has actually touched the robot pet. A program for performing the processing of the flowchart in FIG. 25 may be installed on the robot pet.

Use of "Position (Who is With User)+Amount of Conversation"

Figure 26:
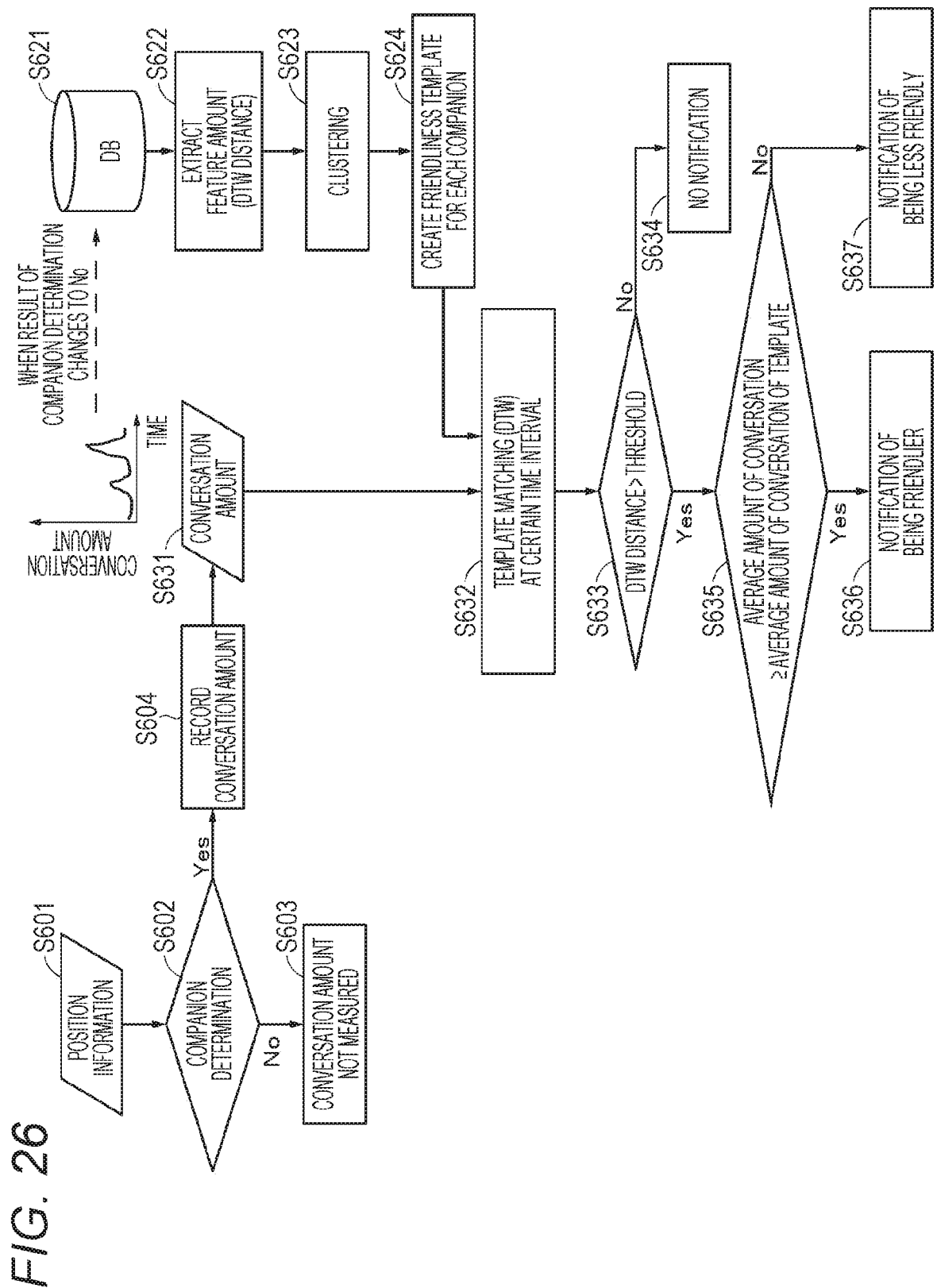
FIG. 26 is a flowchart for describing processing using position information and an amount of conversation.

A mood is visualized on the basis of an increase or decrease in an amount of conversation to provide an opportunity for communication at appropriate times. Processing will be described with reference to FIG. 26.

Step S601: Position information is acquired.

Step S602: A companion determination is made. That is, it is determined whether or not a user is with another person. Position information can be used for the companion determination. Furthermore, other than position information, data such as a state of usage of SNS may be used.

Step S603: If it is determined in step S602 that the user is not with another person, the amount of conversation is not measured.

Step S604: On the other hand, if it is determined in step S603 that the user is with another person, the amount of conversation is recorded. The amount of conversation is recorded only when necessary, and power consumption can be reduced.

Step S621: When the result of the companion determination in step S602 changes to No, a waveform of the amount of conversation is stored in a database. In this case, conversation amount data is accumulated for each companion.

Step S622: A feature amount is extracted from data stored in the database. For example, a DTW distance is calculated, and the DTW distance is extracted as the feature amount.

Step S623: Clustering is performed on the basis of the feature amount.

Step S624: A friendliness template for each companion is created on the basis of a result of the clustering.

Step S631: Data of the amount of conversation of the user with another person is input.

Step S632: A DTW distance between the amount of conversation input at a certain time interval and the daily template created in step S624 is calculated. That is, template matching is performed.

Step S633: It is determined whether or not "DTW distance>threshold" is satisfied.

Step S634: If the condition of step S633 is not satisfied, no notification is given.

Step S635: If the condition of step S633 is satisfied, it is determined whether or not "average amount of conversation average amount of conversation of template" is satisfied.

Figure 27A:
FIGS. 27A, 27B, and 27C are diagrams illustrating an example of a notification given to a user.

Step S636: If the condition of step S635 is satisfied, a notification of being friendlier is given. For example, as illustrated in FIG. 27A, a message "You are being friendlier than usual." is issued.

Figure 27B:
Figure 27C:

Step S637: If the condition of step S635 is not satisfied, a notification of being less friendly is given. For example, as illustrated in FIG. 27B, a message "You are being less friendly than usual. What's the matter?" is issued. The notification is given in real time.

Use of "Position (Staying Place Rareness)+Heart Rate"

Figure 28:
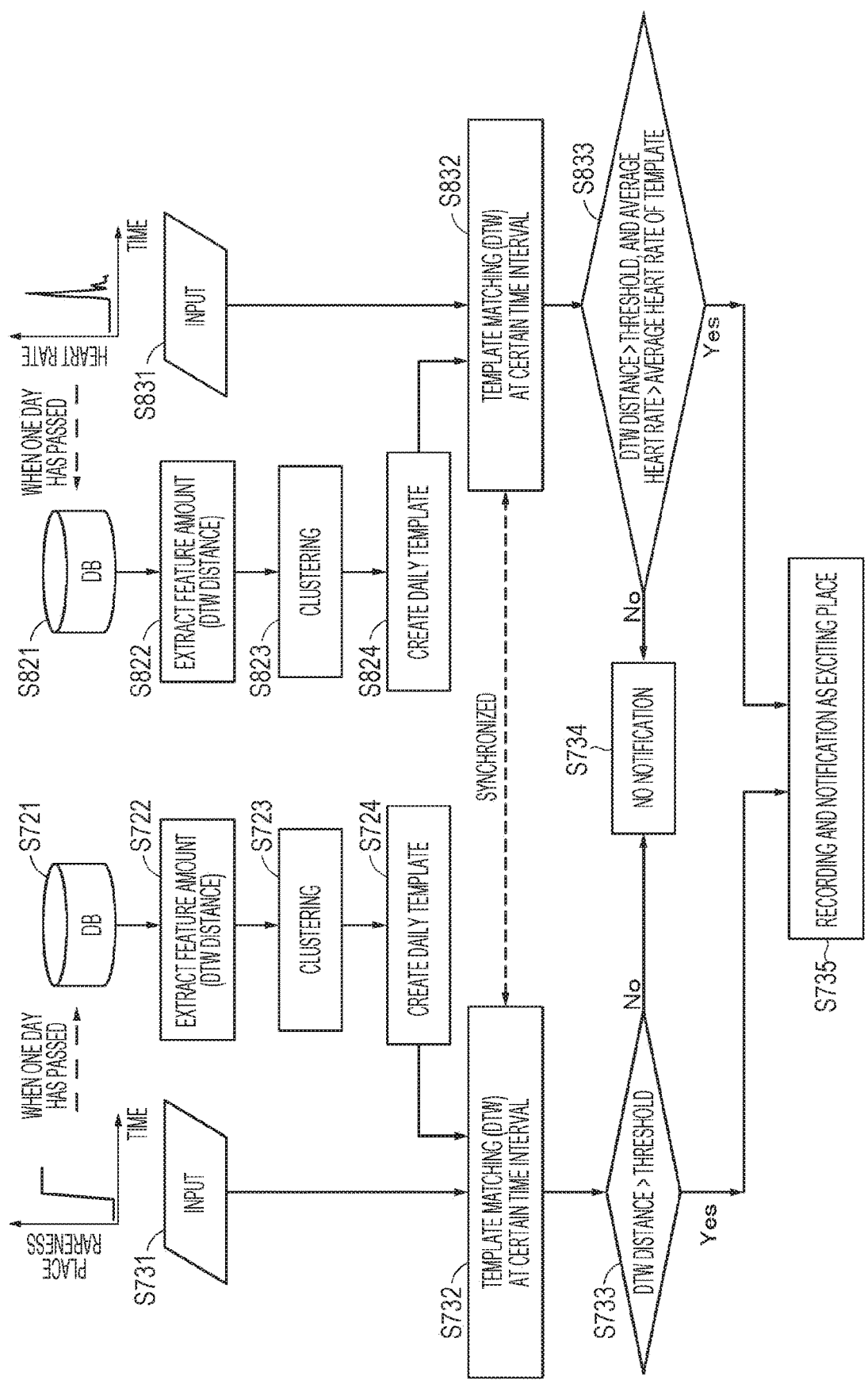
FIG. 28 is a flowchart for describing processing using place rareness and a heart rate.

In this example, exciting place determination can be performed. Processing will be described with reference to FIG. 28.

A determination is made regarding a position (staying place rareness) on a y-axis. Processing after a template has been created (a state where user data has been accumulated to some extent) will be described.

Step S721: For example, a y-axis value is updated at a certain time interval in a day. When one day has passed, a waveform of the day is stored in a database. A horizontal axis of a waveform indicates passage of time, and a vertical axis indicates a y-axis waveform.

Step S722: A feature amount is extracted from data stored in the database. For example, a DTW distance is used as the feature amount.

Step S722: The feature amount is extracted by using a DTW distance.

Step S723: Clustering is performed on the basis of the feature amount.

Step S724: A daily template is created on the basis of a result of the clustering.

Step S731: A y-axis (place rareness) is input from a sensor associated with the user.

Step S732: A DTW distance between an input y-axis value and the daily template created in step S724 is calculated (template matching) at a certain time interval. It is determined that the smaller the DTW distance, the higher the degree of matching.

Step S733: A determination on the DTW distances is made corresponding to each use case. It is determined whether or not "DTW distance>threshold" is satisfied.

Step S734: If the condition of step S733 is not satisfied, no notification is given.

Step S735: The place is recorded as an exciting place, and/or a notification is given. In order for the recording and/or notification to be performed in step S735, it is necessary that conditions of step S833 described later be satisfied.

A determination is made regarding a heart rate on a y-axis. Processing after a template has been created (a state where user data has been accumulated to some extent) will be described.

Step S821: For example, a y-axis value (heart rate) is updated at a certain time interval in a day. When one day has passed, a waveform of the day is stored in a database. A horizontal axis of a waveform indicates passage of time, and a vertical axis indicates a y-axis waveform.

Step S822: A feature amount is extracted from data stored in the database. For example, a DTW distance is calculated.

Step S823: Clustering is performed on the basis of the feature amount.

Step S824: A daily template is created on the basis of a result of the clustering.

Step S831: A y-axis (heart rate) is input from a sensor associated with the user.

Step S832: A DTW distance between an input y-axis value and the daily template created in step S824 is calculated (template matching) at a certain time interval. It is determined that the smaller the DTW distance, the higher the degree of matching. The processing in step S732 (template matching relating to the place rareness) and the processing in step S832 (template matching relating to the heart rate) are assumed to be synchronized in terms of time.

Step S833: A determination on the DTW distances is made corresponding to each use case. It is determined whether or not (DTW distance>threshold) and (average heart rate>average heart rate of template) are both satisfied.

Step S734: If the conditions of step S833 are not satisfied, no notification is given.

If the conditions of step S833 are satisfied, the processing proceeds to step S735.

In step S735, a result of the determination on the place rareness and a result of the determination on the heart rate are given. If both the place rareness and the average heart rate are high, the place is recorded as an exciting place and/or a notification is given.

Combining a plurality of y-axes as in the second embodiment allows for a variety of use cases that can be detected as unusualness.

2. Modified Example

Note that the functions of the processing apparatus in the embodiments described above can be recorded as a program in a recording medium such as a magnetic disk, a magneto-optical disk, or a ROM. It is therefore possible to implement the functions of the information processing apparatus by reading this recording medium with a computer and executing the program with a micro processing unit (MPU), a digital signal processor (DSP), or the like.

Although the embodiments of the present technology have been specifically described above, the present technology is not limited to the above-described embodiments, and various modifications may be made on the basis of the technical idea of the present technology. Furthermore, the configurations, methods, processes, shapes, materials, numerical values, and the like described in the above-described embodiments are merely examples, and configurations, methods, processes, shapes, materials, numerical values, and the like different from those described above may be used where necessary.

Note that the present technology can also be configured as described below.

(1)

An information processing apparatus including:

a processing unit that compares detected time series data and time series data stored in advance to detect unusualness; and a notification unit that controls, when the unusualness is detected by the processing unit, a timing of notification in accordance with a content of the detected unusualness.

(2)

The information processing apparatus according to (1), in which the detected time series data is detected for each object.

(3)

The information processing apparatus according to (2), in which the objects include persons, robots, and animals.

(4)

The information processing apparatus according to any one of (1) to (3), in which a plurality of pieces of the detected time series data is used.

(5)

The information processing apparatus according to any one of (1) to (4), in which the notification unit gives, in a case where the detected unusualness is negative, a notification in accordance with a timing of detection of the unusualness, and gives, in a case where the detected unusualness is positive, a notification after the timing of detection of the unusualness.

(6)

The information processing apparatus according to (1), in which the processing unit performs template forming processing in which a template is formed by clustering on the detected time series data, and determination processing in which a similarity between the detected time series data and the template is determined.

(7)

The information processing apparatus according to (6), in which the template forming processing and the template matching processing are performed in parallel.

(8)

The information processing apparatus according to (6) or (7), in which the template matching processing includes calculating a similarity between the detected time series data and the daily template, and the determination processing includes detecting unusualness on the basis of the similarity.

(9)

The information processing apparatus according to any one of (6) to (8), in which the processing unit performs, on a plurality of pieces of the detected time series data, each of the template forming processing, the template matching processing, and the determination processing, and controls whether to give the notification on the basis of results of a plurality of the determination processing.

(10)

The information processing apparatus according to any one of (6) to (9), in which the template matching processing is performed using a set default value at a stage before the template is formed in the template forming processing.

(11)

An information processing method including:

comparing detected time series data and time series data stored in advance to detect unusualness; and controlling, when the unusualness is detected, a timing of notification in accordance with a content of the detected unusualness.

(12)

A program that causes a computer to execute an information processing method, the information processing method including:

comparing detected time series data and time series data stored in advance to detect unusualness; and controlling, when the unusualness is detected, a timing of notification in accordance with a content of the detected unusualness.

REFERENCE SIGNS LIST

101 Wearable device
102 Sensor unit
103 Notification unit
104 Activity amount data
105 Conversation amount data
106 Position information
201 Sensor unit
301 Unusualness detection processing unit
304 Database

The invention claimed is:

1. An information processing apparatus, comprising:

a database configured to store first data associated with an object in a first time period; and a processor configured to:

acquire second data associated with the object from a plurality of sensors, wherein the acquired second data is associated with the object in a second time period after the first time period, and the plurality of sensors includes a position sensor that detects position data associated with the object, an activity amount sensor that detects an activity amount associated with the object, and a conversation amount detecting sensor that detects conversation amount data associated with the object;

control activation of the conversation amount detecting sensor based on at least one of the detected position data or the detected activity amount, wherein the acquired second data comprises one of the position data or a combination of the position data and the conversation amount data based on the control;
execute a clustering operation on the first data to form a plurality of clusters;
create a template based on a cluster of the plurality of clusters, wherein
a number of elements in the cluster is greater than a number of elements in each cluster of a set of clusters of the plurality of clusters, and
the cluster is different from the set of clusters;
determine a similarity index between the acquired second data and the created template;
detect unusualness based on the determined similarity index; and
control a timing of notification based on a content of the detected unusualness.

2. The information processing apparatus according to claim 1, wherein the processor is further configured to acquire the second data for each object of a plurality of objects.

3. The information processing apparatus according to claim 2, wherein the plurality of objects includes persons, robots, and animals.

4. The information processing apparatus according to claim 1, wherein the processor is further configured to:
provide, based on the detected unusualness is negative, a first notification at a timing of the detection of the unusualness; and
provide, based on the detected unusualness is positive, a second notification after the timing of the detection of the unusualness.

5. The information processing apparatus according to claim 1, wherein the processor is further configured to perform, in parallel, a template forming processing operation associated with the creation of the template and a template matching processing operation associated with the determination of the similarity index.

6. The information processing apparatus according to claim 5, wherein the processor is further configured to:
perform, on a plurality of pieces of the acquired second data, each of the template forming processing operation and the template matching processing operation; and
control a notification based on a result of the template matching processing operation.

7. The information processing apparatus according to claim 5, wherein the processor is further configured to perform the template matching processing operation based on a value at a stage before the template is created in the template forming processing operation.

8. The information processing apparatus according to claim 1, wherein the plurality of sensors further comprises a motion sensor and a biological information sensor.

9. The information processing apparatus according to claim 1, wherein the processor is further configured to:
extract a feature amount from the first data, wherein the feature amount comprises a dynamic time warping distance between a time series waveform of a specific day and each of a plurality of time series waveforms of a plurality of dates; and
execute the clustering operation based on the extracted feature.

10. An information processing method, comprising:
storing, in a database, first data associated with an object in a first time period;
acquiring second data associated with the object from a plurality of sensors, wherein
the acquired second data is associated with the object in a second time period after the first time period, and
the plurality of sensors includes a position sensor that detects position data associated with the object, an activity amount sensor that detects an activity amount associated with the object, and a conversation amount detecting sensor that detects conversation amount data associated with the object;
controlling activation of the conversation amount detecting sensor based on at least one of the detected position data or the detected activity amount, wherein
the acquired second data comprises one of the position data or a combination of the position data and the conversation amount data based on the control;
executing a clustering operation on the first data to form a plurality of clusters;
creating a template based on a cluster of the plurality of clusters, wherein
a number of elements in the cluster is greater than a number of elements in each cluster of a set of clusters of the plurality of clusters, and
the cluster is different from the set of clusters;
determining a similarity index between the acquired second data and the created template;
detecting unusualness based on the determined similarity index; and
controlling a timing of notification based on a content of the detected unusualness.

11. A non-transitory computer-readable medium having stored thereon, computer-executable instructions which, when executed by a processor, cause the processor to execute operations, the operations, comprising:
storing, in a database, first data associated with an object in a first time period;
acquiring second data associated with the object from a plurality of sensors, wherein
the acquired second data is associated with the object in a second time period after the first time period, and
the plurality of sensors includes a position sensor that detects position data associated with the object, an activity amount sensor that detects an activity amount associated with the object, and a conversation amount detecting sensor that detects conversation amount data associated with the object;
controlling activation of the conversation amount detecting sensor based on at least one of the detected position data or the detected activity amount, wherein
the acquired second data comprises one of the position data or a combination of the position data and the conversation amount data based on the control;
executing a clustering operation on the first data to form a plurality of clusters;
creating a template based on a cluster of the plurality of clusters, wherein
a number of elements in the cluster is greater than a number of elements in each cluster of a set of clusters of the plurality of clusters, and
the cluster is different from the set of clusters;
determining a similarity index between the acquired second data and the created template;
detecting unusualness based on the determined similarity index; and
controlling a timing of notification based on a content of the detected unusualness.

* * * * *